(12) United States Patent
Bassi et al.

(10) Patent No.: US 11,944,810 B2
(45) Date of Patent: Apr. 2, 2024

(54) SYSTEMS AND METHODS FOR TRANS-ESOPHAGEAL SYMPATHETIC GANGLION RECRUITMENT

(71) Applicant: Lungpacer Medical Inc., Vancouver (CA)

(72) Inventors: Thiago Gasperini Bassi, Burnaby (CA); Joaquin Andres Hoffer, Anmore (CA); Steven Campbell Reynolds, North Vancouver (CA)

(73) Assignee: Lungpacer Medical Inc., Vancouver (CA)

( * ) Notice: Subject to any disclaimer, the term of this patent is extended or adjusted under 35 U.S.C. 154(b) by 78 days.

(21) Appl. No.: 17/165,231

(22) Filed: Feb. 2, 2021

(65) Prior Publication Data
US 2021/0162205 A1    Jun. 3, 2021

Related U.S. Application Data

(63) Continuation of application No. 16/054,273, filed on Aug. 3, 2018, now Pat. No. 10,940,308.

(Continued)

(51) Int. Cl.
*A61N 1/05* (2006.01)
*A61B 5/03* (2006.01)
(Continued)

(52) U.S. Cl.
CPC ............ *A61N 1/0517* (2013.01); *A61B 5/037* (2013.01); *A61B 5/24* (2021.01); *A61B 5/285* (2021.01);
(Continued)

(58) Field of Classification Search
CPC ........... A61N 1/0517; A61B 3/11; A61B 5/01; A61B 5/026; A61B 5/037; A61B 5/24;
(Continued)

(56) References Cited

U.S. PATENT DOCUMENTS 1,693,734 A    12/1928    Waggoner
2,532,788 A    12/1950    Sarnoff
(Continued)

FOREIGN PATENT DOCUMENTS

CN    1652839 A    8/2005
CN    102143781 A    8/2011
(Continued)

OTHER PUBLICATIONS

Antonica A., et al., "Vagal Control of Lymphocyte Release from Rat Thymus," Journal of the Autonomic Nervous System, Elsevier, vol. 48(3), Aug. 1994, pp. 187-197.
(Continued)

*Primary Examiner* — Carl H Layno
*Assistant Examiner* — Jane C Kalinock
(74) *Attorney, Agent, or Firm* — Bookoff McAndrews, PLLC

(57) ABSTRACT

A method may include positioning a catheter, including at least one electrode, within an esophagus such that the electrode is proximate to at least one sympathetic ganglion. The methods may further include recruiting the sympathetic ganglion via an electrical signal, monitoring the recruitment of the sympathetic ganglion, and, based on the monitoring the recruitment of the sympathetic ganglion, adjusting the electrical signal from the at least one electrode.

18 Claims, 9 Drawing Sheets

Related U.S. Application Data

(60) Provisional application No. 62/541,652, filed on Aug. 4, 2017.

(51) Int. Cl.
| | | |
|---|---|---|
| A61B 5/24 | (2021.01) | |
| A61B 5/285 | (2021.01) | |
| A61B 8/08 | (2006.01) | |
| A61B 18/14 | (2006.01) | |
| *A61B 3/11* | (2006.01) | |
| *A61B 5/00* | (2006.01) | |
| *A61B 5/01* | (2006.01) | |
| *A61B 5/026* | (2006.01) | |
| *A61B 5/369* | (2021.01) | |
| *A61B 8/12* | (2006.01) | |
| *A61B 18/00* | (2006.01) | |

(52) U.S. Cl.
CPC .......... *A61B 8/0808* (2013.01); *A61B 8/0816* (2013.01); *A61B 18/1492* (2013.01); *A61B 3/11* (2013.01); *A61B 5/01* (2013.01); *A61B 5/026* (2013.01); *A61B 5/369* (2021.01); *A61B 5/4233* (2013.01); *A61B 8/12* (2013.01); *A61B 2018/00488* (2013.01)

(58) Field of Classification Search
CPC ....... A61B 5/285; A61B 5/369; A61B 5/4233; A61B 8/0808; A61B 8/0816; A61B 8/12; A61B 18/1492; A61B 2018/00488
USPC .......................................................... 607/40
See application file for complete search history.

(56) References Cited

U.S. PATENT DOCUMENTS

| | | |
|---|---|---|
| 2,664,880 A | 1/1954 | Wales, Jr. |
| 3,348,548 A | 10/1967 | Chardack |
| 3,470,876 A | 10/1969 | John |
| 3,769,984 A | 11/1973 | Muench |
| 3,804,098 A | 4/1974 | Friedman |
| 3,817,241 A | 6/1974 | Grausz |
| 3,835,864 A | 9/1974 | Rasor et al. |
| 3,847,157 A | 11/1974 | Caillouette et al. |
| 3,851,641 A | 12/1974 | Toole et al. |
| 3,896,373 A | 7/1975 | Zelby |
| 3,938,502 A | 2/1976 | Bom |
| 3,983,881 A | 10/1976 | Wickham |
| 4,054,881 A | 10/1977 | Raab |
| 4,072,146 A | 2/1978 | Howes |
| 4,114,601 A | 9/1978 | Abels |
| 4,173,228 A | 11/1979 | Childress et al. |
| 4,249,539 A | 2/1981 | Mezrich et al. |
| 4,317,078 A | 2/1982 | Weed et al. |
| 4,380,237 A | 4/1983 | Newbower |
| 4,407,294 A | 10/1983 | Vilkomerson |
| 4,416,289 A | 11/1983 | Bresler |
| 4,431,005 A | 2/1984 | McCormick |
| 4,431,006 A | 2/1984 | Trimmer et al. |
| 4,445,501 A | 5/1984 | Bresler |
| RE31,873 E | 4/1985 | Howes |
| 4,573,481 A | 3/1986 | Bullara |
| 4,586,923 A | 5/1986 | Gould et al. |
| 4,587,975 A | 5/1986 | Salo et al. |
| 4,643,201 A | 2/1987 | Stokes |
| 4,674,518 A | 6/1987 | Salo |
| 4,681,117 A | 7/1987 | Brodman et al. |
| 4,683,890 A | 8/1987 | Hewson |
| 4,697,595 A | 10/1987 | Breyer et al. |
| 4,706,681 A | 11/1987 | Breyer et al. |
| 4,771,788 A | 9/1988 | Millar |
| 4,819,662 A | 4/1989 | Heil, Jr. et al. |
| 4,827,935 A | 5/1989 | Geddes et al. |
| 4,830,008 A | 5/1989 | Meer |
| 4,840,182 A | 6/1989 | Carlson |
| 4,852,580 A | 8/1989 | Wood |
| 4,860,769 A | 8/1989 | Fogarty et al. |
| 4,905,698 A | 3/1990 | Strohl, Jr. et al. |
| 4,911,174 A | 3/1990 | Pederson et al. |
| 4,934,049 A | 6/1990 | Kiekhafer et al. |
| 4,944,088 A | 7/1990 | Doan et al. |
| 4,951,682 A | 8/1990 | Petre |
| 4,957,110 A | 9/1990 | Vogel et al. |
| 4,989,617 A | 2/1991 | Memberg et al. |
| 5,005,587 A | 4/1991 | Scott |
| 5,036,848 A | 8/1991 | Hewson |
| 5,042,143 A | 8/1991 | Holleman et al. |
| 5,056,519 A | 10/1991 | Vince |
| 5,115,818 A | 5/1992 | Holleman et al. |
| 5,146,918 A | 9/1992 | Kallok et al. |
| 5,170,802 A | 12/1992 | Mehra |
| 5,184,621 A | 2/1993 | Vogel et al. |
| 5,224,491 A | 7/1993 | Mehra |
| 5,243,995 A | 9/1993 | Maier |
| 5,265,604 A | 11/1993 | Vince |
| 5,267,569 A | 12/1993 | Lienhard |
| 5,314,463 A | 5/1994 | Camps et al. |
| 5,316,009 A | 5/1994 | Yamada |
| 5,324,322 A | 6/1994 | Grill, Jr. et al. |
| 5,330,522 A | 7/1994 | Kreyenhagen |
| 5,345,936 A | 9/1994 | Pomeranz et al. |
| 5,383,923 A | 1/1995 | Webster, Jr. |
| 5,411,025 A | 5/1995 | Webster, Jr. |
| 5,417,208 A | 5/1995 | Winkler |
| 5,451,206 A | 9/1995 | Young |
| 5,456,254 A | 10/1995 | Pietroski et al. |
| 5,465,717 A | 11/1995 | Imran et al. |
| 5,476,498 A | 12/1995 | Ayers |
| 5,486,159 A | 1/1996 | Mahurkar |
| 5,507,725 A | 4/1996 | Savage et al. |
| 5,524,632 A | 6/1996 | Stein et al. |
| 5,527,358 A | 6/1996 | Mehmanesh et al. |
| 5,531,686 A | 7/1996 | Lundquist et al. |
| 5,549,655 A | 8/1996 | Erickson |
| 5,555,618 A | 9/1996 | Winkler |
| 5,567,724 A | 10/1996 | Kelleher et al. |
| 5,584,873 A | 12/1996 | Shoberg et al. |
| 5,604,231 A | 2/1997 | Smith et al. |
| 5,665,103 A | 9/1997 | Lafontaine et al. |
| 5,678,535 A | 10/1997 | Dimarco |
| 5,683,370 A | 11/1997 | Luther et al. |
| 5,709,853 A | 1/1998 | Iino et al. |
| 5,716,392 A | 2/1998 | Bourgeois et al. |
| 5,733,255 A | 3/1998 | Dinh et al. |
| 5,755,765 A | 5/1998 | Hyde et al. |
| 5,776,111 A | 7/1998 | Tesio |
| 5,779,732 A | 7/1998 | Amundson |
| 5,782,828 A | 7/1998 | Chen et al. |
| 5,785,706 A | 7/1998 | Bednarek |
| 5,788,681 A | 8/1998 | Weaver et al. |
| 5,813,399 A | 9/1998 | Isaza et al. |
| 5,814,086 A | 9/1998 | Hirschberg et al. |
| RE35,924 E | 10/1998 | Winkler |
| 5,824,027 A | 10/1998 | Hoffer et al. |
| 5,827,192 A | 10/1998 | Gopakumaran et al. |
| 5,916,163 A | 6/1999 | Panescu et al. |
| 5,944,022 A | 8/1999 | Nardella et al. |
| 5,954,761 A | 9/1999 | Machek et al. |
| 5,967,977 A | 10/1999 | Mullis et al. |
| 5,967,978 A | 10/1999 | Littmann et al. |
| 5,971,933 A | 10/1999 | Gopakumaran et al. |
| 5,983,126 A | 11/1999 | Wittkampf |
| 6,006,134 A | 12/1999 | Hill et al. |
| 6,024,702 A | 2/2000 | Iversen |
| 6,096,728 A | 8/2000 | Collins et al. |
| 6,120,476 A | 9/2000 | Fung et al. |
| 6,123,699 A | 9/2000 | Webster, Jr. |
| 6,126,649 A | 10/2000 | Vantassel et al. |
| 6,136,021 A | 10/2000 | Tockman et al. |
| 6,157,862 A | 12/2000 | Brownlee et al. |
| 6,161,029 A | 12/2000 | Spreigl et al. |
| 6,166,048 A | 12/2000 | Bencherif |
| 6,171,277 B1 | 1/2001 | Ponzi |

(56) References Cited

U.S. PATENT DOCUMENTS

| | | | |
|---|---|---|---|
| 6,183,463 B1 | 2/2001 | Webster, Jr. |
| 6,198,970 B1 | 3/2001 | Freed et al. |
| 6,198,974 B1 | 3/2001 | Webster, Jr. |
| 6,201,994 B1 | 3/2001 | Warman et al. |
| 6,208,881 B1 | 3/2001 | Champeau |
| 6,210,339 B1 | 4/2001 | Kiepen et al. |
| 6,212,435 B1 | 4/2001 | Lattner et al. |
| 6,216,045 B1 | 4/2001 | Black et al. |
| 6,236,892 B1 | 5/2001 | Feler |
| 6,240,320 B1 | 5/2001 | Spehr et al. |
| 6,249,708 B1 | 6/2001 | Nelson et al. |
| 6,251,126 B1 | 6/2001 | Ottenhoff et al. |
| 6,269,269 B1 | 7/2001 | Ottenhoff et al. |
| 6,292,695 B1 | 9/2001 | Webster, Jr. et al. |
| 6,295,475 B1 | 9/2001 | Morgan |
| 6,360,740 B1 | 3/2002 | Ward et al. |
| 6,397,108 B1 | 5/2002 | Camps et al. |
| 6,400,976 B1 | 6/2002 | Champeau |
| 6,415,183 B1 | 7/2002 | Scheiner et al. |
| 6,415,187 B1 | 7/2002 | Kuzma et al. |
| 6,438,427 B1 | 8/2002 | Rexhausen et al. |
| 6,445,953 B1 | 9/2002 | Bulkes et al. |
| 6,449,507 B1 | 9/2002 | Hill et al. |
| 6,463,327 B1 | 10/2002 | Lurie et al. |
| 6,493,590 B1 | 12/2002 | Wessman et al. |
| 6,508,802 B1 | 1/2003 | Rosengart et al. |
| 6,526,321 B1 | 2/2003 | Spehr |
| 6,569,114 B2 | 5/2003 | Ponzi et al. |
| 6,584,362 B1 | 6/2003 | Scheiner et al. |
| 6,585,718 B2 | 7/2003 | Hayzelden et al. |
| 6,587,726 B2 | 7/2003 | Lurie et al. |
| 6,602,242 B1 | 8/2003 | Fung et al. |
| 6,610,713 B2 | 8/2003 | Tracey |
| 6,630,611 B1 | 10/2003 | Malowaniec |
| 6,643,552 B2 | 11/2003 | Edell et al. |
| 6,651,652 B1 | 11/2003 | Waard |
| 6,682,526 B1 | 1/2004 | Jones et al. |
| 6,702,780 B1 | 3/2004 | Gilboa et al. |
| 6,718,208 B2 | 4/2004 | Hill et al. |
| 6,721,603 B2 | 4/2004 | Zabara et al. |
| 6,757,970 B1 | 7/2004 | Kuzma et al. |
| 6,778,854 B2 | 8/2004 | Puskas |
| 6,779,257 B2 | 8/2004 | Kiepen et al. |
| 6,844,713 B2 | 1/2005 | Steber et al. |
| RE38,705 E | 2/2005 | Medtronic |
| 6,881,211 B2 | 4/2005 | Schweikert et al. |
| 6,885,888 B2 | 4/2005 | Rezai |
| 6,907,285 B2 | 6/2005 | Denker et al. |
| 6,934,583 B2 | 8/2005 | Weinberg et al. |
| 6,981,314 B2 | 1/2006 | Black et al. |
| 6,999,820 B2 | 2/2006 | Jordan |
| 7,018,374 B2 | 3/2006 | Schon et al. |
| 7,047,627 B2 | 5/2006 | Black et al. |
| 7,071,194 B2 | 7/2006 | Teng |
| 7,072,720 B2 | 7/2006 | Puskas |
| 7,077,823 B2 | 7/2006 | McDaniel |
| 7,082,331 B1 | 7/2006 | Park et al. |
| 7,130,700 B2 | 10/2006 | Gardeski et al. |
| 7,142,903 B2 | 11/2006 | Rodriguez et al. |
| 7,149,585 B2 | 12/2006 | Wessman et al. |
| 7,155,278 B2 | 12/2006 | King et al. |
| 7,168,429 B2 | 1/2007 | Matthews et al. |
| 7,184,829 B2 | 2/2007 | Hill et al. |
| 7,206,636 B1 | 4/2007 | Turcott |
| 7,212,867 B2 | 5/2007 | Van Venrooij et al. |
| 7,225,016 B1 | 5/2007 | Koh |
| 7,225,019 B2 | 5/2007 | Jahns et al. |
| 7,229,429 B2 | 6/2007 | Martin et al. |
| 7,231,260 B2 | 6/2007 | Wallace et al. |
| 7,235,070 B2 | 6/2007 | Vanney |
| 7,269,459 B1 | 9/2007 | Koh |
| 7,277,757 B2 | 10/2007 | Casavant et al. |
| 7,283,875 B2 | 10/2007 | Larsson et al. |
| 7,340,302 B1 | 3/2008 | Falkenberg et al. |
| 7,363,085 B1 | 4/2008 | Benser et al. |
| 7,363,086 B1 | 4/2008 | Koh et al. |
| 7,371,220 B1 | 5/2008 | Koh et al. |
| 7,416,552 B2 | 8/2008 | Paul et al. |
| 7,421,296 B1 | 9/2008 | Benser et al. |
| 7,454,244 B2 | 11/2008 | Kassab et al. |
| 7,519,425 B2 | 4/2009 | Benser et al. |
| 7,519,426 B1 | 4/2009 | Koh et al. |
| 7,522,953 B2 | 4/2009 | Gharib et al. |
| 7,553,305 B2 | 6/2009 | Honebrink et al. |
| 7,555,349 B2 | 6/2009 | Wessman et al. |
| 7,569,029 B2 | 8/2009 | Clark et al. |
| 7,591,265 B2 | 9/2009 | Lee et al. |
| 7,593,760 B2 | 9/2009 | Rodriguez et al. |
| 7,613,524 B2 | 11/2009 | Jordan |
| 7,636,600 B1 | 12/2009 | Koh |
| 7,670,284 B2 | 3/2010 | Padget et al. |
| 7,672,728 B2 | 3/2010 | Libbus et al. |
| 7,672,729 B2 | 3/2010 | Koh et al. |
| 7,676,275 B1 | 3/2010 | Farazi et al. |
| 7,676,910 B2 | 3/2010 | Kiepen et al. |
| 7,697,984 B2 | 4/2010 | Hill et al. |
| 7,747,323 B2 | 6/2010 | Libbus et al. |
| 7,771,388 B2 | 8/2010 | Olsen et al. |
| 7,783,362 B2 | 8/2010 | Whitehurst et al. |
| 7,794,407 B2 | 9/2010 | Rothenberg |
| 7,797,050 B2 | 9/2010 | Libbus et al. |
| 7,813,805 B1 | 10/2010 | Farazi |
| 7,819,883 B2 | 10/2010 | Westlund et al. |
| 7,840,270 B2 | 11/2010 | Ignagni et al. |
| 7,853,302 B2 | 12/2010 | Rodriguez et al. |
| 7,869,865 B2 | 1/2011 | Govari et al. |
| 7,891,085 B1 | 2/2011 | Kuzma et al. |
| 7,925,352 B2 | 4/2011 | Stack et al. |
| 7,949,409 B2 | 5/2011 | Bly et al. |
| 7,949,412 B1 | 5/2011 | Harrison et al. |
| 7,962,214 B2 | 6/2011 | Byerman et al. |
| 7,962,215 B2 | 6/2011 | Ignagni et al. |
| 7,970,475 B2 | 6/2011 | Tehrani et al. |
| 7,972,323 B1 | 7/2011 | Bencini et al. |
| 7,974,693 B2 | 7/2011 | David et al. |
| 7,974,705 B2 | 7/2011 | Zdeblick et al. |
| 7,979,128 B2 | 7/2011 | Tehrani et al. |
| 7,994,655 B2 | 8/2011 | Bauer et al. |
| 8,000,765 B2 | 8/2011 | Rodriguez et al. |
| 8,019,439 B2 | 9/2011 | Kuzma et al. |
| 8,021,327 B2 | 9/2011 | Selkee |
| 8,036,750 B2 | 10/2011 | Caparso et al. |
| 8,050,765 B2 | 11/2011 | Lee et al. |
| 8,052,607 B2 | 11/2011 | Byrd |
| 8,104,470 B2 | 1/2012 | Lee et al. |
| 8,116,872 B2 | 2/2012 | Tehrani et al. |
| 8,121,692 B2 | 2/2012 | Haefner et al. |
| 8,135,471 B2 | 3/2012 | Zhang et al. |
| 8,140,164 B2 | 3/2012 | Tehrani et al. |
| 8,147,486 B2 | 4/2012 | Honour et al. |
| 8,160,701 B2 | 4/2012 | Zhao et al. |
| 8,160,711 B2 | 4/2012 | Tehrani et al. |
| 8,195,297 B2 | 6/2012 | Penner |
| 8,200,336 B2 | 6/2012 | Tehrani et al. |
| 8,206,343 B2 | 6/2012 | Racz |
| 8,224,456 B2 | 7/2012 | Daglow et al. |
| 8,233,987 B2 | 7/2012 | Gelfand et al. |
| 8,233,993 B2 | 7/2012 | Jordan |
| 8,239,037 B2 | 8/2012 | Glenn et al. |
| 8,244,358 B2 | 8/2012 | Tehrani et al. |
| 8,244,359 B2 | 8/2012 | Gelfand et al. |
| 8,244,378 B2 | 8/2012 | Bly et al. |
| 8,255,056 B2 | 8/2012 | Tehrani |
| 8,256,419 B2 | 9/2012 | Sinderby et al. |
| 8,265,736 B2 | 9/2012 | Sathaye et al. |
| 8,265,759 B2 | 9/2012 | Tehrani et al. |
| 8,275,440 B2 | 9/2012 | Rodriguez et al. |
| 8,280,513 B2 | 10/2012 | Tehrani et al. |
| 8,315,713 B2 | 11/2012 | Burnes et al. |
| 8,321,808 B2 | 11/2012 | Goetz et al. |
| 8,335,567 B2 | 12/2012 | Tehrani et al. |
| 8,340,783 B2 | 12/2012 | Sommer et al. |
| 8,348,941 B2 | 1/2013 | Tehrani |
| 8,369,954 B2 | 2/2013 | Stack et al. |

(56) References Cited

U.S. PATENT DOCUMENTS

| | | |
|---|---|---|
| 8,374,704 B2 | 2/2013 | Desai et al. |
| 8,388,541 B2 | 3/2013 | Messerly et al. |
| 8,388,546 B2 | 3/2013 | Rothenberg |
| 8,391,956 B2 | 3/2013 | Zellers et al. |
| 8,401,640 B2 | 3/2013 | Zhao et al. |
| 8,401,651 B2 | 3/2013 | Caparso et al. |
| 8,406,883 B1 | 3/2013 | Barker |
| 8,406,885 B2 | 3/2013 | Ignagni et al. |
| 8,412,331 B2 | 4/2013 | Tehrani et al. |
| 8,412,350 B2 | 4/2013 | Bly |
| 8,428,711 B2 | 4/2013 | Lin et al. |
| 8,428,726 B2 | 4/2013 | Ignagni et al. |
| 8,428,730 B2 | 4/2013 | Stack et al. |
| 8,433,412 B1 | 4/2013 | Westlund et al. |
| 8,442,638 B2 | 5/2013 | Libbus et al. |
| 8,457,764 B2 | 6/2013 | Ramachandran et al. |
| 8,467,876 B2 | 6/2013 | Tehrani |
| 8,473,068 B2 | 6/2013 | Farazi |
| 8,478,412 B2 | 7/2013 | Ignagni et al. |
| 8,478,413 B2 | 7/2013 | Karamanoglu et al. |
| 8,478,426 B2 | 7/2013 | Barker |
| 8,483,834 B2 | 7/2013 | Lee et al. |
| 8,504,158 B2 | 8/2013 | Karamanoglu et al. |
| 8,504,161 B1 | 8/2013 | Kornet et al. |
| 8,509,901 B2 | 8/2013 | Tehrani |
| 8,509,902 B2 | 8/2013 | Cho et al. |
| 8,509,919 B2 | 8/2013 | Yoo et al. |
| 8,512,256 B2 | 8/2013 | Rothenberg |
| 8,522,779 B2 | 9/2013 | Lee et al. |
| 8,527,036 B2 | 9/2013 | Jalde et al. |
| 8,532,793 B2 | 9/2013 | Morris et al. |
| 8,554,323 B2 | 10/2013 | Haefner et al. |
| 8,560,072 B2 | 10/2013 | Caparso et al. |
| 8,560,086 B2 | 10/2013 | Just et al. |
| 8,571,662 B2 | 10/2013 | Hoffer |
| 8,571,685 B2 | 10/2013 | Daglow et al. |
| 8,615,297 B2 | 12/2013 | Sathaye et al. |
| 8,617,228 B2 | 12/2013 | Wittenberger et al. |
| 8,620,412 B2 | 12/2013 | Griffiths et al. |
| 8,620,450 B2 | 12/2013 | Tockman et al. |
| 8,626,292 B2 | 1/2014 | McCabe et al. |
| 8,630,707 B2 | 1/2014 | Zhao et al. |
| 8,644,939 B2 | 2/2014 | Wilson et al. |
| 8,644,952 B2 | 2/2014 | Desai et al. |
| 8,646,172 B2 | 2/2014 | Kuzma et al. |
| 8,650,747 B2 | 2/2014 | Kuzma et al. |
| 8,676,323 B2 | 3/2014 | Ignagni et al. |
| 8,676,344 B2 | 3/2014 | Desai et al. |
| 8,694,123 B2 | 4/2014 | Wahlstrand et al. |
| 8,696,656 B2 | 4/2014 | Abboud et al. |
| 8,706,223 B2 | 4/2014 | Zhou et al. |
| 8,706,235 B2 | 4/2014 | Karamanoglu et al. |
| 8,706,236 B2 | 4/2014 | Ignagni et al. |
| 8,718,763 B2 | 5/2014 | Zhou et al. |
| 8,725,259 B2 | 5/2014 | Kornet et al. |
| 8,738,154 B2 | 5/2014 | Zdeblick et al. |
| 8,755,889 B2 | 6/2014 | Scheiner |
| 8,774,907 B2 | 7/2014 | Rothenberg |
| 8,781,578 B2 | 7/2014 | McCabe et al. |
| 8,781,582 B2 | 7/2014 | Ziegler et al. |
| 8,781,583 B2 | 7/2014 | Cornelussen et al. |
| 8,801,693 B2 | 8/2014 | He et al. |
| 8,805,511 B2 | 8/2014 | Karamanoglu et al. |
| 8,838,245 B2 | 9/2014 | Lin et al. |
| 8,858,455 B2 | 10/2014 | Rothenberg |
| 8,863,742 B2 | 10/2014 | Blomquist et al. |
| 8,886,277 B2 | 11/2014 | Kim et al. |
| 8,897,879 B2 | 11/2014 | Karamanoglu et al. |
| 8,903,507 B2 | 12/2014 | Desai et al. |
| 8,903,509 B2 | 12/2014 | Tockman et al. |
| 8,909,341 B2 | 12/2014 | Gelfand et al. |
| 8,914,113 B2 | 12/2014 | Zhang et al. |
| 8,918,169 B2 | 12/2014 | Kassab et al. |
| 8,918,987 B2 | 12/2014 | Kuzma et al. |
| 8,923,971 B2 | 12/2014 | Haefner et al. |
| 8,942,823 B2 | 1/2015 | Desai et al. |
| 8,942,824 B2 | 1/2015 | Yoo et al. |
| 8,948,884 B2 | 2/2015 | Ramachandran et al. |
| 8,968,299 B2 | 3/2015 | Kauphusman et al. |
| 8,972,015 B2 | 3/2015 | Stack et al. |
| 8,983,602 B2 | 3/2015 | Sathaye et al. |
| 9,008,775 B2 | 4/2015 | Sathaye et al. |
| 9,026,231 B2 | 5/2015 | Hoffer |
| 9,037,264 B2 | 5/2015 | Just et al. |
| 9,042,981 B2 | 5/2015 | Yoo et al. |
| 9,072,864 B2 | 7/2015 | Putz |
| 9,072,899 B1 | 7/2015 | Nickloes |
| 9,108,058 B2 | 8/2015 | Hoffer |
| 9,108,059 B2 | 8/2015 | Hoffer |
| 9,125,578 B2 | 9/2015 | Grunwald |
| 9,138,580 B2 | 9/2015 | Ignagni et al. |
| 9,138,585 B2 | 9/2015 | Saha et al. |
| 9,149,642 B2 | 10/2015 | McCabe et al. |
| 9,168,377 B2 | 10/2015 | Hoffer |
| 9,205,258 B2 | 12/2015 | Simon et al. |
| 9,216,291 B2 | 12/2015 | Lee et al. |
| 9,220,898 B2 | 12/2015 | Hoffer |
| 9,226,688 B2 | 1/2016 | Jacobsen et al. |
| 9,226,689 B2 | 1/2016 | Jacobsen et al. |
| 9,242,088 B2 | 1/2016 | Thakkar et al. |
| 9,259,573 B2 | 2/2016 | Tehrani et al. |
| 9,295,846 B2 | 3/2016 | Westlund et al. |
| 9,314,618 B2 | 4/2016 | Imran et al. |
| 9,333,363 B2 | 5/2016 | Hoffer et al. |
| 9,345,422 B2 | 5/2016 | Rothenberg |
| 9,370,657 B2 | 6/2016 | Tehrani et al. |
| 9,398,931 B2 | 7/2016 | Wittenberger et al. |
| 9,415,188 B2 | 8/2016 | He et al. |
| 9,427,566 B2 | 8/2016 | Reed et al. |
| 9,427,588 B2 | 8/2016 | Sathaye et al. |
| 9,474,894 B2 | 10/2016 | Mercanzini et al. |
| 9,485,873 B2 | 11/2016 | Shah et al. |
| 9,498,625 B2 | 11/2016 | Bauer et al. |
| 9,498,631 B2 | 11/2016 | Demmer et al. |
| 9,504,837 B2 | 11/2016 | Demmer et al. |
| 9,532,724 B2 | 1/2017 | Grunwald et al. |
| 9,533,160 B2 | 1/2017 | Brooke et al. |
| 9,539,429 B2 | 1/2017 | Brooke et al. |
| 9,545,511 B2 | 1/2017 | Thakkar et al. |
| 9,561,369 B2 | 2/2017 | Burnes et al. |
| 9,566,436 B2 | 2/2017 | Hoffer et al. |
| 9,572,982 B2 | 2/2017 | Burnes et al. |
| 9,597,509 B2 | 3/2017 | Hoffer et al. |
| 9,615,759 B2 | 4/2017 | Hurezan et al. |
| 9,623,252 B2 | 4/2017 | Sathaye et al. |
| 9,662,494 B2 | 5/2017 | Young et al. |
| 9,682,235 B1 | 6/2017 | O'Mahony et al. |
| 9,694,185 B2 | 7/2017 | Bauer |
| 9,717,899 B2 | 8/2017 | Kuzma et al. |
| 9,724,018 B2 | 8/2017 | Cho et al. |
| 9,744,351 B1 | 8/2017 | Gelfand et al. |
| 9,776,005 B2 | 10/2017 | Meyyappan et al. |
| 9,833,623 B2 | 12/2017 | Gnanashanmugam et al. |
| 9,861,817 B2 | 1/2018 | Cho et al. |
| 9,872,989 B2 | 1/2018 | Jung et al. |
| 9,884,178 B2 | 2/2018 | Bouton et al. |
| 9,884,179 B2 | 2/2018 | Bouton et al. |
| 9,919,149 B2 | 3/2018 | Imran et al. |
| 9,931,504 B2 | 4/2018 | Thakkar et al. |
| 9,950,167 B2 | 4/2018 | Hoffer et al. |
| 9,956,396 B2 | 5/2018 | Young et al. |
| 9,968,785 B2 | 5/2018 | Hoffer et al. |
| 9,968,786 B2 | 5/2018 | Bauer et al. |
| 9,999,767 B2 * | 6/2018 | Tal .............. A61N 1/0517 |
| 10,065,037 B2 * | 9/2018 | Nelson .......... A61N 1/0551 |
| 2001/0052345 A1 | 12/2001 | Niazi |
| 2002/0026228 A1 | 2/2002 | Schauerte |
| 2002/0056454 A1 | 5/2002 | Samzelius |
| 2002/0065544 A1 | 5/2002 | Smits et al. |
| 2002/0087156 A1 | 7/2002 | Maguire et al. |
| 2002/0128546 A1 | 9/2002 | Silver |
| 2002/0188325 A1 | 12/2002 | Hill et al. |
| 2003/0078623 A1 | 4/2003 | Weinberg et al. |
| 2003/0195571 A1 | 10/2003 | Burnes et al. |

(56) References Cited

U.S. PATENT DOCUMENTS

| | | |
|---|---|---|
| 2004/0003813 A1 | 1/2004 | Banner et al. |
| 2004/0010303 A1 | 1/2004 | Bolea et al. |
| 2004/0030362 A1 | 2/2004 | Hill et al. |
| 2004/0044377 A1 | 3/2004 | Larsson et al. |
| 2004/0064069 A1 | 4/2004 | Reynolds et al. |
| 2004/0077936 A1 | 4/2004 | Larsson et al. |
| 2004/0088015 A1 | 5/2004 | Casavant et al. |
| 2004/0111139 A1 | 6/2004 | McCreery |
| 2004/0186543 A1 | 9/2004 | King et al. |
| 2004/0210261 A1 | 10/2004 | King et al. |
| 2005/0004565 A1 | 1/2005 | Vanney |
| 2005/0013879 A1 | 1/2005 | Lin et al. |
| 2005/0021102 A1 | 1/2005 | Ignagni et al. |
| 2005/0027338 A1 | 2/2005 | Hill |
| 2005/0033136 A1 | 2/2005 | Govari et al. |
| 2005/0033137 A1 | 2/2005 | Oral et al. |
| 2005/0043765 A1 | 2/2005 | Williams et al. |
| 2005/0065567 A1 | 3/2005 | Lee et al. |
| 2005/0070981 A1 | 3/2005 | Verma |
| 2005/0075578 A1 | 4/2005 | Gharib et al. |
| 2005/0085865 A1 | 4/2005 | Tehrani |
| 2005/0085866 A1 | 4/2005 | Tehrani |
| 2005/0085867 A1 | 4/2005 | Tehrani et al. |
| 2005/0085868 A1 | 4/2005 | Tehrani et al. |
| 2005/0085869 A1 | 4/2005 | Tehrani et al. |
| 2005/0096710 A1 | 5/2005 | Kieval |
| 2005/0109340 A1 | 5/2005 | Tehrani |
| 2005/0113710 A1 | 5/2005 | Stahmann et al. |
| 2005/0115561 A1 | 6/2005 | Stahmann et al. |
| 2005/0131485 A1 | 6/2005 | Knudson et al. |
| 2005/0138791 A1 | 6/2005 | Black et al. |
| 2005/0138792 A1 | 6/2005 | Black et al. |
| 2005/0143787 A1 | 6/2005 | Boveja et al. |
| 2005/0165457 A1 | 7/2005 | Benser et al. |
| 2005/0182454 A1 | 8/2005 | Gharib et al. |
| 2005/0187584 A1 | 8/2005 | Denker et al. |
| 2005/0192655 A1 | 9/2005 | Black et al. |
| 2005/0251238 A1 | 11/2005 | Wallace et al. |
| 2005/0251239 A1 | 11/2005 | Wallace et al. |
| 2005/0288728 A1 | 12/2005 | Libbus et al. |
| 2005/0288730 A1 | 12/2005 | Deem et al. |
| 2006/0030894 A1 | 2/2006 | Tehrani |
| 2006/0035849 A1 | 2/2006 | Spiegelman et al. |
| 2006/0058852 A1 | 3/2006 | Koh et al. |
| 2006/0074449 A1 | 4/2006 | Denker et al. |
| 2006/0122661 A1 | 6/2006 | Mandell |
| 2006/0122662 A1 | 6/2006 | Tehrani et al. |
| 2006/0130833 A1 | 6/2006 | Younes |
| 2006/0142815 A1 | 6/2006 | Tehrani et al. |
| 2006/0149334 A1 | 7/2006 | Tehrani et al. |
| 2006/0155222 A1 | 7/2006 | Sherman et al. |
| 2006/0167523 A1 | 7/2006 | Tehrani et al. |
| 2006/0188325 A1 | 8/2006 | Dolan |
| 2006/0195159 A1 | 8/2006 | Bradley et al. |
| 2006/0217791 A1 | 9/2006 | Spinka et al. |
| 2006/0224209 A1 | 10/2006 | Meyer |
| 2006/0229677 A1 | 10/2006 | Moffitt et al. |
| 2006/0247729 A1 | 11/2006 | Tehrani et al. |
| 2006/0253161 A1 | 11/2006 | Libbus et al. |
| 2006/0253182 A1 | 11/2006 | King |
| 2006/0258667 A1 | 11/2006 | Teng |
| 2006/0259107 A1 | 11/2006 | Caparso et al. |
| 2006/0282131 A1 | 12/2006 | Caparso et al. |
| 2006/0287679 A1 | 12/2006 | Stone |
| 2007/0005053 A1 | 1/2007 | Dando |
| 2007/0021795 A1 | 1/2007 | Tehrani |
| 2007/0027448 A1 | 2/2007 | Paul et al. |
| 2007/0087314 A1 | 4/2007 | Gomo |
| 2007/0093875 A1 | 4/2007 | Chavan et al. |
| 2007/0106357 A1 | 5/2007 | Denker et al. |
| 2007/0112402 A1 | 5/2007 | Grill et al. |
| 2007/0112403 A1 | 5/2007 | Moffitt et al. |
| 2007/0118183 A1 | 5/2007 | Gelfand et al. |
| 2007/0150006 A1 | 6/2007 | Libbus et al. |
| 2007/0168007 A1 | 7/2007 | Kuzma et al. |
| 2007/0173900 A1 | 7/2007 | Siegel et al. |
| 2007/0191908 A1 | 8/2007 | Jacob et al. |
| 2007/0196780 A1 | 8/2007 | Ware et al. |
| 2007/0203549 A1 | 8/2007 | Demarais et al. |
| 2007/0208388 A1 | 9/2007 | Jahns et al. |
| 2007/0221224 A1 | 9/2007 | Pittman et al. |
| 2007/0240718 A1 | 10/2007 | Daly |
| 2007/0250056 A1 | 10/2007 | Vanney |
| 2007/0250162 A1 | 10/2007 | Royalty |
| 2007/0255379 A1 | 11/2007 | Williams et al. |
| 2007/0265611 A1 | 11/2007 | Ignagni et al. |
| 2007/0288076 A1 | 12/2007 | Bulkes et al. |
| 2008/0039916 A1 | 2/2008 | Colliou et al. |
| 2008/0065002 A1 | 3/2008 | Lobl et al. |
| 2008/0125828 A1 | 5/2008 | Ignagni et al. |
| 2008/0161878 A1 | 7/2008 | Tehrani et al. |
| 2008/0167695 A1 | 7/2008 | Tehrani et al. |
| 2008/0177347 A1 | 7/2008 | Tehrani et al. |
| 2008/0183186 A1 | 7/2008 | Bly et al. |
| 2008/0183187 A1 | 7/2008 | Bly |
| 2008/0183239 A1 | 7/2008 | Tehrani et al. |
| 2008/0183240 A1 | 7/2008 | Tehrani et al. |
| 2008/0183253 A1 | 7/2008 | Bly |
| 2008/0183254 A1 | 7/2008 | Bly et al. |
| 2008/0183255 A1 | 7/2008 | Bly et al. |
| 2008/0183259 A1 | 7/2008 | Bly et al. |
| 2008/0183264 A1 | 7/2008 | Bly et al. |
| 2008/0183265 A1 | 7/2008 | Bly et al. |
| 2008/0188903 A1 | 8/2008 | Tehrani et al. |
| 2008/0215106 A1 | 9/2008 | Lee et al. |
| 2008/0269834 A1 | 10/2008 | Byerman et al. |
| 2008/0269840 A1* | 10/2008 | Scott ............... A61N 1/0517 607/60 |
| 2008/0288010 A1 | 11/2008 | Tehrani et al. |
| 2008/0288015 A1 | 11/2008 | Tehrani et al. |
| 2008/0312712 A1 | 12/2008 | Penner |
| 2008/0312725 A1 | 12/2008 | Penner |
| 2009/0024047 A1 | 1/2009 | Shipley et al. |
| 2009/0036947 A1 | 2/2009 | Westlund et al. |
| 2009/0118785 A1 | 5/2009 | Ignagni et al. |
| 2009/0275956 A1 | 11/2009 | Burnes et al. |
| 2009/0275996 A1 | 11/2009 | Burnes et al. |
| 2009/0276022 A1 | 11/2009 | Burnes et al. |
| 2010/0022950 A1 | 1/2010 | Anderson et al. |
| 2010/0036451 A1 | 2/2010 | Hoffer |
| 2010/0042193 A1* | 2/2010 | Slavin ............ A61N 1/36017 607/117 |
| 2010/0077606 A1 | 4/2010 | Black et al. |
| 2010/0094376 A1 | 4/2010 | Penner |
| 2010/0114227 A1 | 5/2010 | Cholette |
| 2010/0114254 A1 | 5/2010 | Kornet |
| 2010/0114261 A1 | 5/2010 | Errico et al. |
| 2010/0198296 A1 | 8/2010 | Ignagni et al. |
| 2010/0204766 A1 | 8/2010 | Zdeblick et al. |
| 2010/0268311 A1 | 10/2010 | Cardinal et al. |
| 2010/0319691 A1 | 12/2010 | Lurie et al. |
| 2011/0060381 A1 | 3/2011 | Ignagni et al. |
| 2011/0077726 A1 | 3/2011 | Westlund et al. |
| 2011/0118815 A1 | 5/2011 | Kuzma et al. |
| 2011/0230932 A1 | 9/2011 | Tehrani et al. |
| 2011/0230935 A1 | 9/2011 | Zdeblick |
| 2011/0230945 A1 | 9/2011 | Ohtaka et al. |
| 2011/0270358 A1 | 11/2011 | Davis et al. |
| 2011/0288609 A1 | 11/2011 | Tehrani et al. |
| 2011/0313330 A1 | 12/2011 | Loushin et al. |
| 2012/0035684 A1 | 2/2012 | Thompson et al. |
| 2012/0053654 A1 | 3/2012 | Tehrani et al. |
| 2012/0078320 A1 | 3/2012 | Schotzko et al. |
| 2012/0130217 A1 | 5/2012 | Kauphusman et al. |
| 2012/0158091 A1 | 6/2012 | Tehrani et al. |
| 2012/0209284 A1 | 8/2012 | Westlund et al. |
| 2012/0215278 A1 | 8/2012 | Penner |
| 2012/0323293 A1 | 12/2012 | Tehrani et al. |
| 2013/0018247 A1 | 1/2013 | Glenn et al. |
| 2013/0018427 A1 | 1/2013 | Pham et al. |
| 2013/0023972 A1 | 1/2013 | Kuzma et al. |
| 2013/0030496 A1 | 1/2013 | Karamanoglu et al. |
| 2013/0030497 A1 | 1/2013 | Karamanoglu et al. |
| 2013/0030498 A1 | 1/2013 | Karamanoglu et al. |

(56) References Cited

U.S. PATENT DOCUMENTS

| | | |
|---|---|---|
| 2013/0060245 A1 | 3/2013 | Grunewald et al. |
| 2013/0116743 A1 | 5/2013 | Karamanoglu et al. |
| 2013/0123891 A1 | 5/2013 | Swanson |
| 2013/0131743 A1 | 5/2013 | Yamasaki et al. |
| 2013/0158514 A1 | 6/2013 | Elia et al. |
| 2013/0158625 A1 | 6/2013 | Gelfand et al. |
| 2013/0165989 A1 | 6/2013 | Gelfand et al. |
| 2013/0167372 A1 | 7/2013 | Black et al. |
| 2013/0197601 A1 | 8/2013 | Tehrani et al. |
| 2013/0237906 A1 | 9/2013 | Park et al. |
| 2013/0268018 A1 | 10/2013 | Brooke et al. |
| 2013/0289686 A1 | 10/2013 | Masson et al. |
| 2013/0296964 A1 | 11/2013 | Tehrani |
| 2013/0296973 A1 | 11/2013 | Tehrani et al. |
| 2013/0296977 A1 | 11/2013 | Chiu et al. |
| 2013/0317587 A1 | 11/2013 | Barker |
| 2013/0333696 A1 | 12/2013 | Lee et al. |
| 2014/0067032 A1 | 3/2014 | Morris et al. |
| 2014/0088580 A1 | 3/2014 | Wittenberger et al. |
| 2014/0114371 A1 | 4/2014 | Westlund et al. |
| 2014/0121716 A1 | 5/2014 | Casavant et al. |
| 2014/0128953 A1 | 5/2014 | Zhao et al. |
| 2014/0148780 A1 | 5/2014 | Putz |
| 2014/0288384 A1 | 9/2014 | Mulrooney |
| 2014/0316486 A1 | 10/2014 | Zhou et al. |
| 2014/0324115 A1 | 10/2014 | Ziegler et al. |
| 2014/0378803 A1 | 12/2014 | Geistert et al. |
| 2015/0018839 A1 | 1/2015 | Morris et al. |
| 2015/0034081 A1 | 2/2015 | Tehrani et al. |
| 2015/0045810 A1 | 2/2015 | Hoffer et al. |
| 2015/0045848 A1 | 2/2015 | Cho et al. |
| 2015/0119950 A1 | 4/2015 | Demmer et al. |
| 2015/0165207 A1 | 6/2015 | Karamanoglu |
| 2015/0196354 A1 | 7/2015 | Haverkost et al. |
| 2015/0196356 A1 | 7/2015 | Kauphusman et al. |
| 2015/0202448 A1 | 7/2015 | Hoffer et al. |
| 2015/0231348 A1 | 8/2015 | Lee et al. |
| 2015/0250982 A1 | 9/2015 | Osypka et al. |
| 2015/0265833 A1 | 9/2015 | Meyyappan et al. |
| 2015/0283340 A1 | 10/2015 | Zhang et al. |
| 2015/0290476 A1 | 10/2015 | Krocak et al. |
| 2015/0359487 A1 | 12/2015 | Coulombe |
| 2015/0374252 A1 | 12/2015 | De et al. |
| 2015/0374991 A1 | 12/2015 | Morris et al. |
| 2016/0001072 A1 | 1/2016 | Gelfand et al. |
| 2016/0144078 A1 | 5/2016 | Young et al. |
| 2016/0193460 A1 | 7/2016 | Xu et al. |
| 2016/0228696 A1 | 8/2016 | Imran et al. |
| 2016/0239627 A1 | 8/2016 | Cerny et al. |
| 2016/0256692 A1 | 9/2016 | Baru |
| 2016/0310730 A1 | 10/2016 | Martins et al. |
| 2016/0331326 A1 | 11/2016 | Xiang et al. |
| 2016/0367815 A1 | 12/2016 | Hoffer |
| 2017/0007825 A1 | 1/2017 | Thakkar et al. |
| 2017/0013713 A1 | 1/2017 | Shah et al. |
| 2017/0021166 A1 | 1/2017 | Bauer et al. |
| 2017/0028191 A1 | 2/2017 | Mercanzini et al. |
| 2017/0036017 A1 | 2/2017 | Tehrani et al. |
| 2017/0050033 A1 | 2/2017 | Wechter |
| 2017/0143973 A1 | 5/2017 | Tehrani |
| 2017/0143975 A1 | 5/2017 | Hoffer et al. |
| 2017/0196503 A1 | 7/2017 | Narayan et al. |
| 2017/0224993 A1 | 8/2017 | Sathaye et al. |
| 2017/0232250 A1 | 8/2017 | Kim et al. |
| 2017/0252558 A1 | 9/2017 | O'Mahony et al. |
| 2017/0291023 A1 | 10/2017 | Kuzma et al. |
| 2017/0296812 A1 | 10/2017 | O'Mahony et al. |
| 2017/0312006 A1 | 11/2017 | McFarlin et al. |
| 2017/0312507 A1 | 11/2017 | Bauer et al. |
| 2017/0312508 A1 | 11/2017 | Bauer et al. |
| 2017/0312509 A1 | 11/2017 | Bauer et al. |
| 2017/0326359 A1 | 11/2017 | Gelfand et al. |
| 2017/0347921 A1 | 12/2017 | Haber et al. |
| 2018/0001086 A1 | 1/2018 | Bartholomew et al. |
| 2018/0008821 A1 | 1/2018 | Gonzalez et al. |
| 2018/0110562 A1 | 4/2018 | Govari et al. |
| 2018/0117334 A1 | 5/2018 | Jung |

FOREIGN PATENT DOCUMENTS

| | | |
|---|---|---|
| EP | 0993840 A1 | 4/2000 |
| EP | 1304135 A2 | 4/2003 |
| EP | 0605796 B1 | 8/2003 |
| EP | 2489395 A1 | 8/2012 |
| FR | 2801509 A1 | 6/2001 |
| JP | H08510677 A | 11/1996 |
| JP | 2003503119 A | 1/2003 |
| JP | 2010516353 A | 5/2010 |
| JP | 2011200571 A | 10/2011 |
| JP | 2012000195 A | 1/2012 |
| WO | WO-9407564 A2 | 4/1994 |
| WO | WO-9508357 A1 | 3/1995 |
| WO | WO-9964105 A1 | 12/1999 |
| WO | WO-9965561 A1 | 12/1999 |
| WO | WO-0100273 A1 | 1/2001 |
| WO | WO-02058785 A1 | 8/2002 |
| WO | WO-03094855 A1 | 11/2003 |
| WO | WO-2006110338 A1 | 10/2006 |
| WO | WO-2006115877 A1 | 11/2006 |
| WO | WO-2007053508 A1 | 5/2007 |
| WO | WO-2008092246 A1 | 8/2008 |
| WO | WO-2008094344 A1 | 8/2008 |
| WO | WO-2009006337 A1 | 1/2009 |
| WO | WO-2009134459 A2 | 11/2009 |
| WO | WO-2010029842 A1 | 3/2010 |
| WO | WO-2010148412 A1 | 12/2010 |
| WO | WO-2011158410 A1 | 12/2011 |
| WO | WO-2012106533 A2 | 8/2012 |
| WO | WO-2013131187 A1 | 9/2013 |
| WO | WO-2013188965 A1 | 12/2013 |
| WO | WO-2014008171 A1 | 1/2014 |
| WO | WO-2015075548 A1 | 5/2015 |
| WO | WO-2015109401 A1 | 7/2015 |

OTHER PUBLICATIONS

Ayas N.T., et al., "Prevention of Human Diaphragm Atrophy with Short periods of Electrical Stimulation," American Journal of Respiratory and Critical Care Medicine, Jun. 1999, vol. 159(6), pp. 2018-2020.

Borovikova, et al., "Role of the Vagus Nerve in the Anti-Inflammatory Effects of CNI-1493," Proceedings of the Annual Meeting of Professional Research Scientists: Experimental Biology 2000, Abstract 97.9, Apr. 15-18, 2000.

Borovikova L.V., et al., "Role of Vagus Nerve Signaling in CNI-1493-Mediated Suppression of Acute Inflammation," Autonomic Neuroscience: Basic and Clinical, vol. 85 (1-3), Dec. 20, 2000, pp. 141-147.

Borovikova L.V., et al., "Vagus Nerve Stimulation Attenuates the Systemic Inflammatory Response to Endotoxin," Nature, Macmillan Magazines Ltd, vol. 405, May 25, 2000, pp. 458-462.

Chinese Search Report for Application No. CN2013/80023357.5, dated Jul. 24, 2015.

Co-pending U.S. Appl. No. 15/606,867, filed May 26, 2017.

Daggeti, W.M. et al., "Intracaval Electrophrenic Stimulation. I. Experimental Application during Barbiturate Intoxication Hemorrhage and Gang," Journal of Thoracic and Cardiovascular Surgery, 1966, vol. 51 (5), pp. 676-884.

Daggeti, W.M. et al., "Intracaval electrophrenic stimulation. II. Studies on Pulmonary Mechanics Surface Tension Urine Flow and Bilateral Ph," Journal of Thoracic and Cardiovascular Surgery, 1970, vol. 60(1 ), pp. 98-107.

De Gregorio, M.A et al., "The Gunther Tulip Retrievable Filter: Prolonged Temporary Filtration by Repositioning within the Inferior Vena Cava," Journal of Vascular and Interventional Radiology, 2003, vol. 14, pp. 1259-1265.

Deng Y-J et al., "The Effect of Positive Pressure Ventilation Combined with Diaphragm Pacing on Respiratory Mechanics in Patients

(56) References Cited

OTHER PUBLICATIONS with Respiratory Failure; Respiratory Mechanics," Chinese critical care medicine, Apr. 2011, vol. 23(4), pp. 213-215.
Escher, Doris J.W. et al., "Clinical Control of Respiration by Transvenous Phrenic Pacing," American Society for Artificial Internal Organs: Apr. 1968—vol. 14—Issue 1—pp. 192-197.
European Search Report for Application No. 13758363, dated Nov. 12, 2015.
European Search Report for Application No. EP17169051.4, dated Sep. 8, 2017, 7 pages.
Extended European Search Report for Application No. 14864542.7, dated Jun. 2, 2017, 8 pages.
Extended European Search Report for Application No. 15740415.3, dated Jul. 7, 2017.
Fleshner M., et al., "Thermogenic and Corticosterone Responses to Intravenous Cytokines (IL-1β and TNF-α) are Attenuated by Subdiaphragmatic Vagotomy," Journal of Neuroimmunology, vol. 86, Jun. 1998, pp. 134-141.
Frisch S., "A Feasibility Study of a Novel Minimally Invasive Approach for Diaphragm Pacing," Master of Science Thesis, Simon Fraser University, 2009, p. 148.
Furman, S., "Transvenous Stimulation of the Phrenic Nerves," Journal of Thoracic and Cardiovascular Surgery, 1971, vol. 62 (5), pp. 743-751.
Gaykema R.P.A. et al., "Subdiaphragmatic Vagotomy Suppresses Endotoxin-Induced Activation of Hypothalamic Corticotropin-Releasing Hormone Neurons and ACTH Secretion," Endocrinology, The Endocrine Society, vol. 136 (10), 1995, pp. 4717-4720.
Gupta A.K., "Respiration Rate Measurement Based on Impedance Pneumography," Data Acquisition Products, Texas Instruments, Application Report, SBAA181, Feb. 2011, 11 pages.
Guslandi M., "Nicotine Treatment for Ulcerative Colitis," The British Journal of Clinical Pharmacology, Blackwell Science Ltd, vol. 48, 1999, pp. 481-484.
Hoffer J.A. et al., "Diaphragm Pacing with Endovascular Electrodes", IFESS 2010—International Functional Electrical Stimulation Society, 15th Anniversary Conference, Vienna, Austria, Sep. 2010.
Huffman, William J. et al., "Modulation of Neuroinflammation and Memory Dysfunction Using Percutaneous Vagus Nerve Stimulation in Mice," Brain Stimulation, 2018.
Ishii, K. et al., "Effects of Bilateral Transvenous Diaphragm Pacing on Hemodynamic Function in Patients after Cardiac Operations," J. Thorac. Cardiovasc. Surg., 1990.
Japanese Office Action in corresponding Japanese Application No. 2014-560202, dated Dec. 6, 2016, 4 pages.
Japanese Office Action in corresponding Japanese Application No. 2014-560202, dated Oct. 17, 2017, 5 pages.
Kawashima K., et al., "Extraneuronal Cholinergic System in Lymphocytes," Pharmacology & Therapeutics, Elsevier, vol. 86, 2000, pp. 29-48.
Levine S., et al., "Rapid disuse atrophy of diaphragm fibers in mechanically ventilated humans," New England Journal of Medicine, 2008, vol. 358, pp. 1327-1335.
Lungpacer: Therapy, News.< http://lungpacer.com>. Accessed Dec. 27, 2016.
Madretsma, G.S., et al., "Nicotine Inhibits the In-vitro Production of Interleukin 2 and Tumour Necrosis Factor-α by Human Mononuclear Cells," Immunopharmacology, Elsevier, vol. 35 (1), Oct. 1996, pp. 47-51.
Marcy, T.W. et al., "Diaphragm Pacing for Ventilatory Insufficiency," Journal of Intensive Care Medicine, 1987, vol. 2 (6), pp. 345-353.
Meyyappan R., "Diaphragm Pacing during Controlled Mechanical Ventilation: Pre-Clinical Observations Reveal A Substantial Improvement In Respiratory Mechanics", 17th Biennial Canadian Biomechanics Society Meeting, Burnaby, BC, Jun. 6-9, 2012.
Nabutovsky, Y., et al., "Lead Design and Initial Applications of a New Lead for Long-Term Endovascular Vagal Stimulation," PACE, Blackwell Publishing, Inc, vol. 30(1), Jan. 2007, pp. S215-S218.

Notification of Reasons for Rejection and English language translation issued in corresponding Japanese Patent Application No. 2015-517565, dated Mar. 28, 2017, 6 pages.
Onders R.,, "A Diaphragm Pacing as a Short-Term Assist to Positive Pressure Mechanical Ventilation in Critical Care Patients," Chest, Oct. 24, 2007, vol. 132(4), pp. 5715-5728.
Onders R.,, "Diaphragm Pacing for Acute Respiratory Failure," Difficult Decisions in Thoracic Surgery, Chapter 37, Springer-Verlag, 2011, M.K. Ferguson (ed.), pp. 329-335.
Onders R, et al., "Diaphragm Pacing with Natural Orifice Transluminal Endoscopic Surgery: Potential for Difficult-To-Wean Intensive Care Unit Patients," Surgical Endoscopy, 2007, vol. 21, pp. 475-479.
Pavlovic D., et al., "Diaphragm Pacing During Prolonged Mechanical Ventilation of the Lungs could Prevent from Respiratory Muscle Fatigue," Medical Hypotheses, vol. 60 (3), 2003, pp. 398-403.
Planas R.F., et al., "Diaphragmatic Pressures: Transvenous vs. Direct Phrenic Nerve Stimulation," Journal of Applied Physiology, vol. 59(1), 1985, pp. 269-273.
Romanovsky, A.A., et al., "The Vagus Nerve in the Thermoregulatory Response to Systemic Inflammation," American Journal of Physiology, vol. 273 (1 Pt 2), 1997, pp. R407-R413.
Salmela L., et al., "Verification of the Position of a Central Venous Catheter by Intra-Atrial ECG. When does this method fail?," Acta Anasthesiol Scand, vol. 37 (1), 1993, pp. 26-28.
Sandborn W.J., "Transdermal Nicotine for Mildly to Moderately Active Ulcerative Colitis," Annals of Internal Medicine, vol. 126 (5), Mar. 1, 1997, pp. 364-371.
Sandoval R., "A Catch/Ike Property-Based Stimulation Protocol for Diaphragm Pacing", Master of Science Coursework project, Simon Fraser University, Mar. 2013.
Sarnoff, S.J. et al., "Electrophrenic Respiration," Science, 1948, vol. 108, p. 482.
Sato E., et al., "Acetylcholine Stimulates Alveolar Macrophages to Release Inflammatory Cell Chemotactic Activity," American Journal of Physiology, vol. 274 (Lung Cellular and Molecular Physiology 18), 1998, pp. L970-L979.
Sato, K.Z., et al., "Diversity of mRNA Expression for Muscarinic Acetylcholine Receptor Subtypes and Neuronal Nicotinic Acetylcholine Receptor Subunits in Human Mononuclear Leukocytes and Leukemic Cell Lines," Neuroscience Letters, vol. 266 (1), 1999, pp. 17-20.
Schauerte P., et al., "Transvenous Parasympathetic Nerve Stimulation in the Inferior Vena Cava and Atrioventricular Conduction," Journal of Cardiovascular Electrophysiology, vol. 11 (1), Jan. 2000, pp. 64-69.
Schauerte P.N., et al., "Transvenous Parasympathetic Cardiac Nerve Stimulation: An Approach for Stable Sinus Rate Control," Journal of Cardiovascular Electrophysiology, vol. 10 (11), Nov. 1999, pp. 1517-1524.
Scheinman R.I., et al., "Role of Transcriptional Activation of IKBa in Mediation of Immunosuppression by Glucocorticoids," Science, vol. 270, Oct. 13, 1995, pp. 283-286.
Sher, M.E., et al., "The Influence of Cigarette Smoking on Cytokine Levels in Patients with Inflammatory Bowel Disease," Inflammatory Bowel Diseases, vol. 5 (2), May 1999, pp. 73-78.
Steinlein, O., "New Functions for Nicotinic Acetylcholine Receptors?," Behavioural Brain Research, vol. 95, 1998, pp. 31-35.
Sternberg E.M., (Series Editor) "Neural-Immune Interactions in Health and Disease," The Journal of Clinical Investigation, vol. 100 (11), Dec. 1997, pp. 2641-2647.
Sykes., A.P., et al., "An Investigation into the Effect and Mechanisms of Action of Nicotine in Inflammatory Bowel Disease," Inflammation Research, vol. 49, 2000, pp. 311-319.
Toyabe S., et al., "Identification of Nicotinic Acetylcholine Receptors on Lymphocytes in the Periphery as well as Thymus in Mice," Immunology, vol. 92, 1997, pp. 201-205.
Van Dijk A.P.M., et al., "Transdermal Nicotine Inhibits Interleukin 2 Synthesis by Mononuclear Cells Derived from Healthy Volunteers," European Journal of Clinical Investigation, vol. 28, 1998, pp. 664-671.
Wanner, A. et al., "Trasvenous Phrenic Nerve Stimulation in Anesthetized Dogs," Journal of Applied Physiology, 1973, vol. 34 (4), pp. 489-494.

(56) References Cited

OTHER PUBLICATIONS

Watkins L.R., et al., "Blockade of Interleukin-1 Induced Hyperthermia by Subdiaphragmatic Vagotomy: Evidence for Vagal Mediation of Immune-Brain Communication," Neuroscience Letters, vol. 183, 1995, pp. 27-31.

Watkins L.R., et al., "Implications of Immune-to-Brain Communication for Sickness and Pain," PNAS (Proceedings of the National Academy of Sciences of the USA), vol. 96 (14), Jul. 6, 1999, pp. 7710-7713.

Whaley K., et al., "C2 Synthesis by Human Monocytes is Modulated by a Nicotinic Cholinergic Receptor," Nature, vol. 293, Oct. 15, 1981, pp. 580-582 (and reference page).

PCT Search Report dated Oct. 26, 2018 for PCT Application No. PCT/IB2018/000603, 7 pages.

PCT Search Report and Written Opinion dated Oct. 17, 2018 for PCT Application No. PCT/US2018/043661, 13 pages.

\* cited by examiner

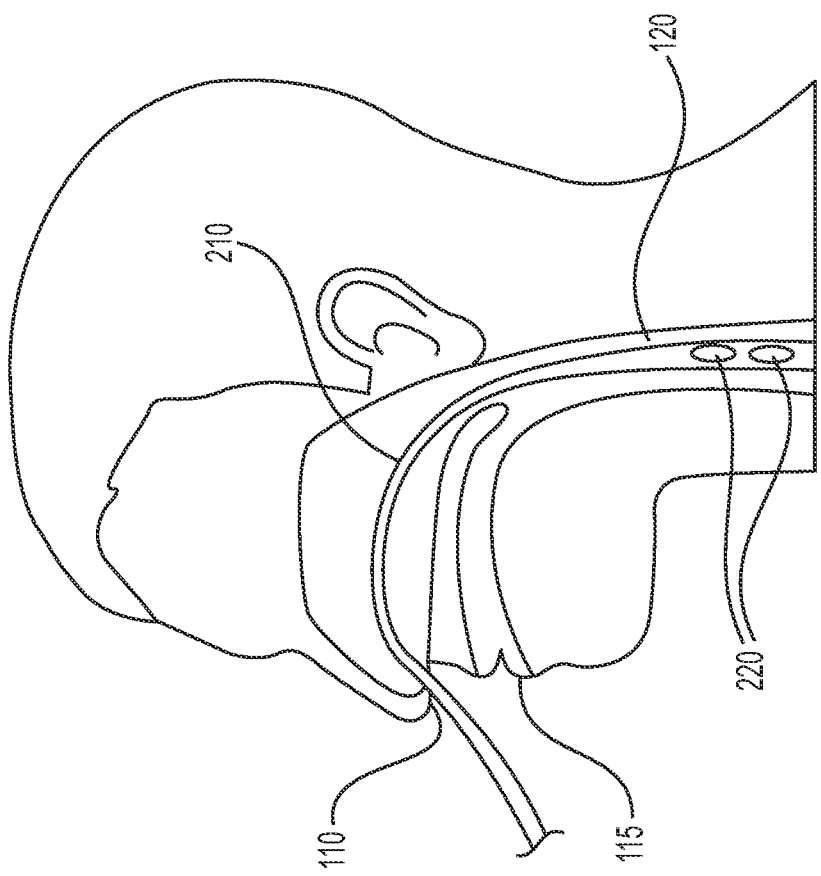

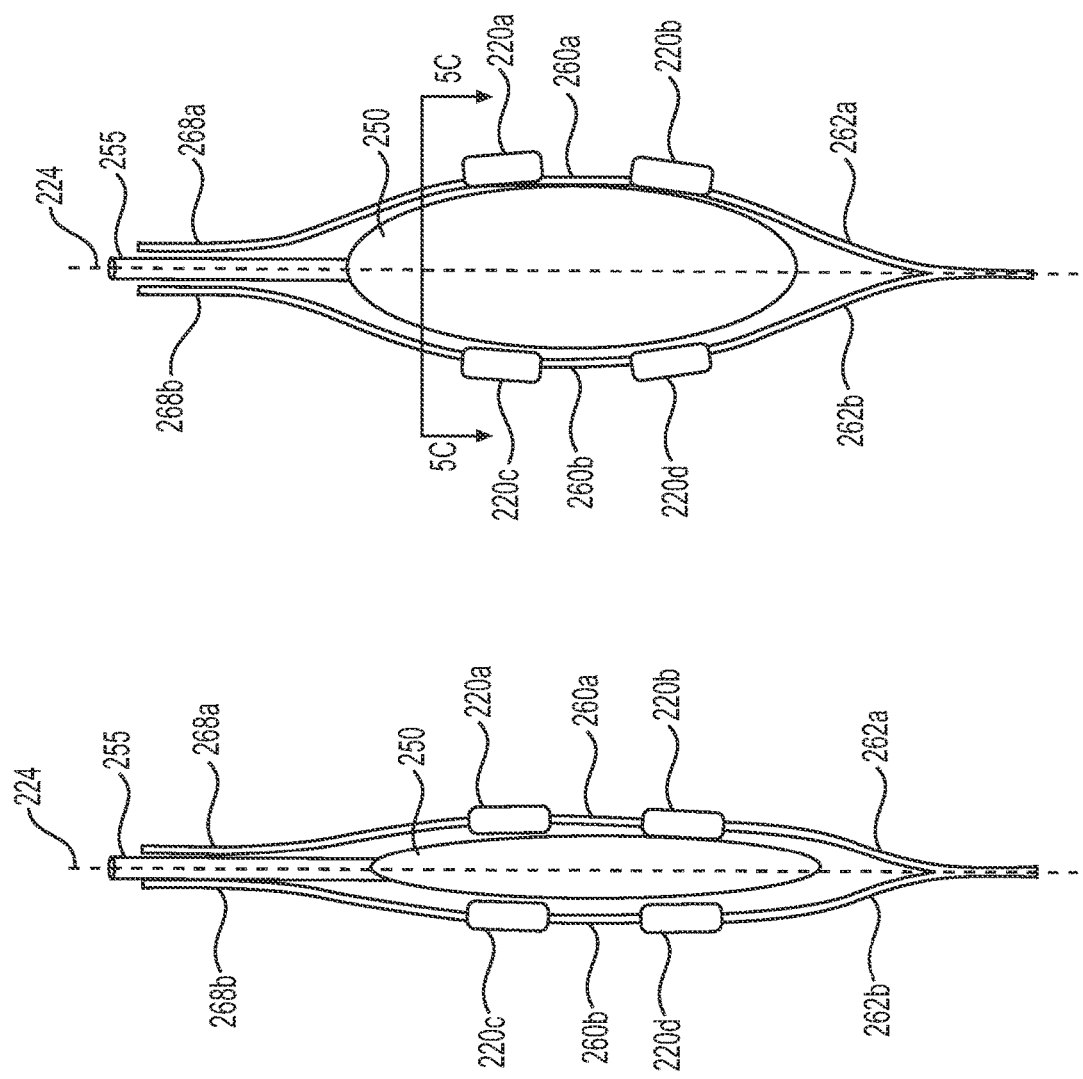
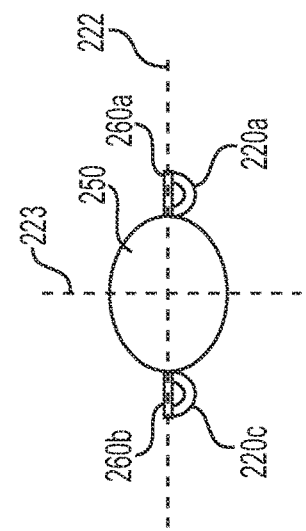
FIG. 5A
FIG. 5B
FIG. 5C

SYSTEMS AND METHODS FOR TRANS-ESOPHAGEAL SYMPATHETIC GANGLION RECRUITMENT

CROSS-REFERENCE TO RELATED APPLICATION(S)

This application is a continuation of U.S. patent application Ser. No. 16/054,273, filed on Aug. 3, 2018, now U.S. Pat. No. 10,940,308, which claims priority to U.S. Provisional Application No. 62/541,652, filed on Aug. 4, 2017, the entire disclosures of both of which are hereby incorporated by reference in their entirety.

In general, all publications, patent applications, and patents mentioned in this specification are herein incorporated by reference in their entirety to the same extent as if each individual document was specifically individually indicated to be incorporated by reference.

TECHNICAL FIELD

The embodiments of this disclosure generally relate to methods, systems, and devices for the diagnosis, mitigation, and treatment of neural injury (e.g., aneurism, stroke, concussion, etc.). In some examples, the present disclosure is directed to a method of reducing the occurrence of brain cell damage or death of a patient. One exemplary aspect is directed to a method of reducing the occurrence of brain cell damage or death caused by a transient cerebral hypoxia/ischemia condition, a brain inflammation condition, or a traumatic brain injury (TBI) event. Another exemplary aspect is directed to devices, systems, and methods for reducing brain and/or cognitive injury in patients diagnosed with a subarachnoid hemorrhage (SAH).

BACKGROUND

SAH is characterized by bleeding into the space between the arachnoid membrane and the pia mater of the brain. SAH may occur as a result of a head injury or as a consequence of a cerebral aneurysm. The worldwide incidence of SAH has been estimated to be 7-25 per 100,000 person-years; from 1% to 7% of cerebrovascular accidents (CVAs, e.g., strokes) are the result of SAH. In some instances, SAH may result in delayed cerebral ischemia associated with a cerebral vasospasm (CVS). Studies have estimated 33% to 46% of patients with SAH will experience a clinically relevant CVS. Further, the delayed cerebral ischemia resulting from an SAH-related CVS may significantly impair a patient's functionality and quality of life, with only 20% of patients leaving the hospital with their pre-CVA neurological status.

Without being limited by theory, it is believed the combination of intracerebral hemorrhage and raised intracranial pressure may lead to an over-activation of the sympathetic system leading to an increased risk of CVS. This over-activation is thought to occur through two mechanisms, a direct effect on the medulla that leads to activation of the descending sympathetic nervous system and a local release of inflammatory mediators that circulate to the peripheral circulation where they activate the sympathetic system. The over-activation of the sympathetic system may result in a release of adrenaline, a sudden increase in blood pressure, increased contractility of the ventricle system, increased vasoconstriction, and/or increased systemic vascular resistance. Over-activation of the sympathetic system can result in cardiac arrhythmias, electrocardiographic changes, and/or cardiac arrest that may occur rapidly after the onset of hemorrhage. In some cases, a neurogenic pulmonary edema may develop which is characterized by increased pressure within the pulmonary circulation, leading to leaking of fluid from the pulmonary capillaries into the air spaces of the lung.

To limit the negative consequences resulting from SAH, physicians have experimented with sympathetic ganglion blocks in an attempt to prevent an over-activation of the sympathetic system. For example, an anesthetic may be delivered to the sympathetic ganglia via hypodermic needle using ultrasound visualization, fluoroscopy, or computed tomography (CT) scanning. In one procedure, a needle is inserted between the trachea and carotid sheath. In another procedure, a needle is inserted rostral to the sternoclavicular junction. Such invasive techniques involving the insertion of a needle into the neck and/or near the trachea are associated with the development of pneumothorax. Further, these techniques require large, immobile, and/or expensive imaging equipment and procedures, such as, for example, ultrasound visualization, fluoroscopy, or CT scanning.

Such procedures require specialized training, large-scale equipment and/or imagery machinery, and may only be performed in few hospitals with specialized staff. Further, such approaches are limited in the regions of cervical sympathetic ganglia that may be blocked due to the invasive nature of such procedures, the proximity of nerves, vasculature, and trachea, and the imprecision of anesthetic blocks. Additionally, the feasibility of using such techniques as a preventive measure is uncertain. The local anesthetics used in such blocks may last only several hours, while the increased risk of a delayed CVS may last up to 14 days after the SAH. Further, the long-term consequences of continued use of such anesthetics as nerve blocking agents are not yet known and are potentially severe.

SUMMARY

Embodiments of the present disclosure relate to, among other things, systems, devices, and methods for treating, including preventing and moderating, brain injury. Each of the embodiments disclosed herein may include one or more of the features described in connection with any of the other disclosed embodiments.

This disclosure includes methods of treatment. In some aspects, the methods may include positioning a catheter within the esophagus, the catheter including at least one electrode, wherein the catheter is positioned so that the at least one electrode is proximate to at least one sympathetic ganglion. The methods may further include recruiting the sympathetic ganglion via an electrical signal from the at least one electrode. This may include recruiting at least one of a left stellate ganglion or a right stellate ganglion via the electrical signal from the at least one electrode. The recruiting of the sympathetic ganglion may include blocking the transmission of nerve signals along the sympathetic ganglion.

In some examples, the methods may further include where at least one electrode includes a plurality of electrodes. A first electrode of the plurality of electrodes may be positioned on a surface opposite a second electrode of the plurality of electrodes, where the first electrode and second electrode are positioned at the same axial level. In some aspects, an electrical signal may be transmitted by the plurality of electrodes to recruit the left stellate ganglion and the right stellate ganglion. In some examples, at least one electrode is positioned inferior to the C4 vertebra and superior to the T2 vertebra. In some aspects, a method may include positioning a catheter including at least four electrodes. The catheter may be positioned through an oroesophageal or a nasoesophageal cavity.

In some examples of methods, the electrical signal is pulsed and has a frequency of 100 Hz to 100 kHz and an amplitude of 10 µA to 20 mA. The methods may further include monitoring the recruitment of the sympathetic ganglia. The monitoring may include observing palpebral droop, performing an electroencephalogram, measuring pupil diameter, observing a color change in a sclera, measuring a skin temperature, measuring a skin perspiration, performing a transcranial Doppler ultrasonogram, or a combination thereof. In some aspects, based on the monitoring the recruitment of the sympathetic ganglia, the methods may further comprise adjusting the electrical signal from at least one electrode.

In further aspects, systems for treatment may include an esophageal catheter, one or more sensors for sensing a physiologic parameter indicative of a state of the sympathetic ganglia, and a controller in communication with the at least one electrode and the one or more sensors, where, upon receiving a first signal from the one or more sensors based on the sensed physiological parameter, the controller induces the at least one electrode to transmit an electrical signal that recruit the sympathetic ganglia. In some examples, the esophageal catheter comprises at least one electrode configured to be positioned within the esophagus proximate to at least one sympathetic ganglion. The one or more sensors may measure or monitor pupil dilation, skin temperature, skin perspiration, blood flow, electroencephalography, or a combination thereof. In other aspects, upon receiving a second signal from the one or more sensors, the controller induces the at least one electrode to cease transmitting the electrical signal or the controller induces the at least one electrode to adjust one or more of the amplitude or frequency of the transmitted electrical signal.

In some examples, the at least one electrode of the systems includes a plurality of electrodes configured to independently transmit electrical signals and a first electrode of the plurality of electrodes is configured to be positioned proximate to a left stellate ganglion and a second electrode of the plurality of electrodes is configured to be positioned proximate to a right stellate ganglion. In some aspects, upon receiving a second signal from one or more sensors, the controller may induce one of the plurality of electrodes to adjust one or more of the amplitude or frequency of the electrical signal.

In further examples, an esophageal catheter may include an intermediate section operable to radially expand from a contracted state to an expanded state, a plurality of electrodes, and/or a feeding tube. At least two of the plurality of electrodes are farther displaced when the intermediate section is in an expanded state. The intermediate section may include an inflatable member. In some embodiments, the intermediate section may comprise at least two arms. The at least two arms may be connected by a tether and each arm may include a joined end, a proximal end, and at least one electrode positioned between the joined and the proximal end. The joined end may connect to the joined end of one or more other arms and the proximal end may be farther displaced from the proximal end of one or more other arms when the intermediate section is in an expanded state as compared to when the intermediate section is in a contracted state.

BRIEF DESCRIPTION OF DRAWINGS

The accompanying drawings, which are incorporated in and constitute a part of this specification, illustrate non-limiting embodiments of the present disclosure and together with the description serve to explain the principles of the disclosure.

FIG. 1A illustrates the anatomy of selected tissues and anatomical lumens in a person's head and neck, along with an exemplary esophageal catheter placed within the esophagus, according to one or more embodiments of the present disclosure;

FIG. 5A illustrates a perspective view of an esophageal catheter in a contracted state, according to one or more embodiments of the present disclosure;

FIG. 5B illustrates a perspective view of the esophageal catheter shown in FIG. 5A, in an expanded state;

FIG. 5C illustrates a cross-sectional view depicting the esophageal catheter in an expanded state shown in FIG. 5B, along line 5C-5C of FIG. 5B;

DETAILED DESCRIPTION

Figure 1B:
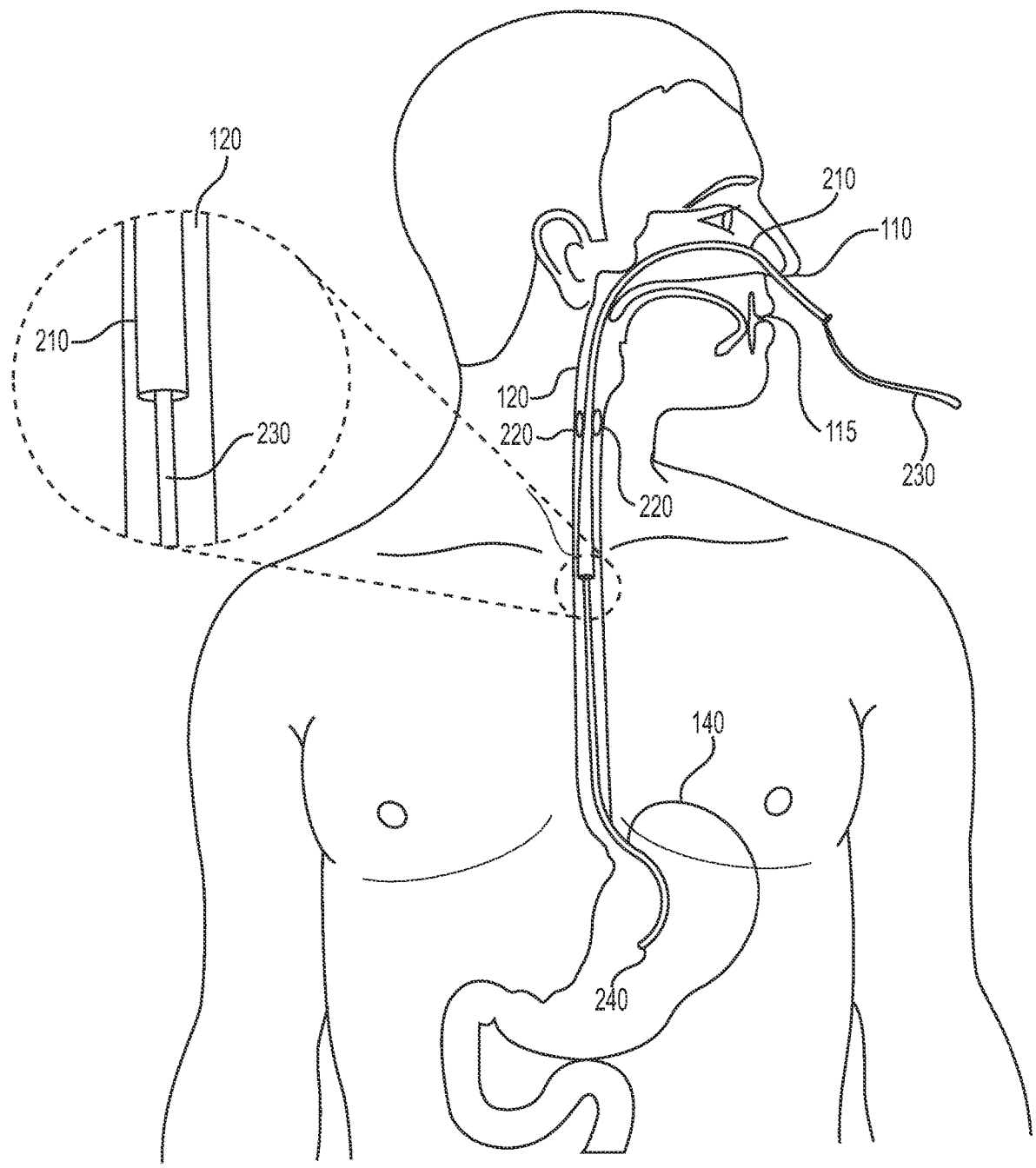
FIG. 1B illustrates the anatomy of selected tissues, anatomical lumens, and organs in a person's head, neck, and torso, along with an exemplary esophageal catheter placed within the esophagus, according to one or more embodiments of the present disclosure.

Throughout the following description, specific details are set forth to provide a more thorough understanding to persons skilled in the art. The following description of examples of the technology is not intended to be exhaustive or to limit the system to the precise forms of any example embodiment. Accordingly, the description and drawings are to be regarded in an illustrative sense, rather than a restrictive sense.

Further aspects of the disclosures and features of example embodiments are illustrated in the appended drawings and/or described in the text of this specification and/or described in the accompanying claims. It may be understood that both the foregoing general description and the following detailed description are exemplary and explanatory only and are not restrictive of the invention, as claimed. As used herein, the terms "comprises," "comprising," "including," "having," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−15% of a stated value.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively further away from the operator using the medical device or insertion device, or closer to the interior of the body.

One or more embodiments may relate to a device and/or method to deliver transesophageal neuromodulation to a cervical or thoracic sympathetic ganglion (e.g., a stellate ganglion) in order to increase brain perfusion. Given the proximity of the esophagus to target cervical sympathetic ganglia, an esophageal catheter including electrodes may be deployed within the esophagus to delivery high-frequency (e.g., greater than or equal to 1 kHz) electrical signals (e.g., electrical pulse trains).

In general, embodiments of this disclosure relate to systems, medical devices, and methods for recruiting sympathetic ganglia and preventing, modulating, controlling, or treating injury (e.g., injury of the brain). For example, the injury may be caused or enhanced by a TBI event. As used herein, the term "injury" may refer to an alteration in cellular or molecular integrity, activity, level, robustness, state, or other alteration that is traceable to an event. For example, brain injury may be neuronal injury resulting from stress (repetitive stress), inflammation, oxidative stress, disease, pain, stroke, and/or physical injury such as surgery or trauma (e.g., a TBI event). An SAH or a resulting CVS may exacerbate, worsen, or cause a brain injury. One or more methods herein may relate to treating and monitoring patients with an SAH to prevent or reduce incidence of a delayed CVS. Further, one or more methods herein may be applied to improve outcomes in patients with an acute stroke or a traumatic brain injury. Recruitment of at least one sympathetic ganglion may control, reduce or mitigate inflammation from ischemia or traumatic brain injury that may cause secondary injury to neurons.

In one or more embodiments, recruiting a nerve may include blocking the transmission of nerve signals along one or more cells (e.g. neurons). Recruiting a nerve may include transmitting an electrical signal (e.g., a recruitment signal) to the nerve that interferes with the transmission of a normal nerve signal. In some aspects, recruiting a nerve may be an ongoing process via the transmission of a repeating, pulsed, electrical signal to the nerve. The repeating, pulsed, electrical signal may stop axonal conduction of nerve signals. In instances, a nerve receiving an ongoing recruitment signal may be considered recruited. In some embodiments, a nerve which is unable to conduct nerve signals may be considered recruited. Ceasing the recruitment of a nerve may be referred to herein as releasing the nerve. Similarly, a nerve that is no longer recruited, but was once recruited, may be referred to as released.

In one or more embodiments, a method of treatment comprises positioning a catheter including at least one electrode within an esophagus such that the at least one electrode is proximate to at least one sympathetic ganglion, and recruiting the at least one sympathetic ganglion via an electrical signal from the at least one electrode. At least one electrode may be positioned inferior to the C4 vertebrae and superior to the T2 vertebrae and/or along the dorsal wall of the esophagus. In some embodiments at least one electrode may be positioned inferior to the C5 vertebrae and superior to the T1 vertebrae. Alternatively or in addition, at least one electrode is positioned 20 centimeters (cm) to 27 cm from the edge of the nasogastric cavity. Further, recruiting at least one sympathetic ganglia may include recruiting one or more of the left stellate ganglion or the right stellate ganglion. In some embodiments, recruiting at least one sympathetic ganglia may including blocking the transmission of nerve signals along the sympathetic ganglia, such as, for example, along the left stellate ganglion or along the right stellate ganglion. In some embodiments, recruitment of the left stellate ganglion may be used in patients presenting with cardiac indications and/or upper left limb pain. In other embodiments, recruitment of the right stellate ganglion may be used in patients with cardiac arrhythmias. The recruitment of both the left stellate ganglion and the right stellate ganglion may be used to treat patients presenting with cardiac arrhythmias such as, for example, ventricular arrhythmia.

The methods may further include monitoring, sensing, and/or testing one or more functions, activity, or other parameters of the brain or nervous system, obtaining the results of the sensing or tests, and analyzing these results, for example, to determine the effect of the transmitted electrical signal on nervous function and/or activity. Based on the test results and their analysis, parameters (e.g., timing, duration, profile, and/or intensity) for the electrical signal may be generated or modified, and one or more nerves may be recruited or released based on the parameters. In some cases, the methods may include testing nervous function and the status of one or more nerve recruitments. Exemplary tests on the status of nerve (e.g., sympathetic ganglia) recruitments include detection of electrodermal activity, monitoring heart rate variability, evaluating responses related to the control of pupil diameter and blood flow to the eye, measuring peripheral blood flow (e.g., via transcranial Doppler ultrasonogram), heart rate and blood pressure variability analysis, thermoregulatory sweat test, magnetic resonance imaging (MM, e.g., functional MM), single-photon emission computed tomography (SPECT), evaluation of electroencephalography (EEG) waveforms, the measurement of visual, audio and somatosensory evoked potentials, changes in absolute vital sign values, and changes in pain threshold. The tests may also include detecting chemistry (e.g., levels and activities of proteins or other molecules such as inflammation- or pain-related molecules) in the blood or other bodily fluids. The chemistry tests may include measuring the level and/concentrations of TNF-α, other cytokines, serotonin, gastrin, norepinephrine, and/or other hormones. For example, methods of the present disclosure may include monitoring the recruitment of the sympathetic ganglia by observing palpebral droop, performing an electroencephalogram, measuring pupil diameter, observing a color change in the sclera, measuring skin temperature, performing a transcranial Doppler ultrasonogram, or a combination thereof.

The tests of nerve recruitment may be performed prior to, during, or after an electrical signal is transmitted or at different stages of recruitment signal transmission. For example, the tests may be performed before, during, or after a transmitted electrical signal (e.g., before, during, or after one or more periods of a pulsed electrical signal). Alternatively or in addition, the tests may be performed before, during, or after recruitment of a nerve. Brain function and/or sympathetic ganglia recruitment status or activity may be determined based on the test results. The results from the tests performed at different times may be compared to each other or to reference threshold values or ranges, e.g. thresholds or ranges that indicate normal nervous function or other levels of nervous function. In such cases, brain function and/or sympathetic ganglia recruitment status may be determined based on the comparisons.

For a patient receiving or having received treatment via an electrical signal from an esophageal catheter, the brain function and/or sympathetic ganglia recruitment status in the patient may be detected and compared to parameters indicative of normal function and/or status of the brain and/or the nerves. If a difference or a significant difference is determined, one or more parameters of the electrical signal transmitted by at least one electrode may be modified to adjust the recruitment of the sympathetic ganglia. The adjustment may be performed continuously (e.g., based on real-time monitoring of brain function and/or sympathetic ganglion recruitment status) for delivering optimal and personalized therapy to the patient.

In one or more embodiments, monitoring the recruitment of a nerve (e.g. sympathetic ganglia) may include monitoring the palpebral droop or slump of a patient. When transmission of nerve signals through the sympathetic ganglia is blocked (e.g., when the sympathetic ganglia is recruited) one or more superior eyelids of a patient may droop, slump or distend further from its normal open position. In some instances, blocking the transmission of nerve signals through the left stellate ganglion may cause the left superior eyelid to droop. Additionally or in the alternative, blocking the transmission of nerve signals through the right stellate ganglion may cause the right superior eyelid to droop. Monitoring the palpebral droop of a patient (e.g., observing whether either or both superior eyelids are drooping) may inform a controller and/or a user (e.g., physician or patient) of the recruitment status of one or more nerves, such as, for example, the sympathetic ganglia (e.g., left stellate ganglion and/or right stellate ganglion). As described herein, when a physiological parameter (e.g., palpebral droop) is observed and/or monitored, the observation may be made by one or more sensors and/or a user (e.g., patient, physician, nurse, or other healthcare professional). The one or more sensors and/or users may transmit the observation to a controller, in some embodiments.

In one or more embodiments, monitoring the recruitment of a nerve (e.g. sympathetic ganglia) may include monitoring the brain activity of a patient via an electroencephalogram (EEG). Generally, an EEG records the electrical activity of a brain via electrodes placed along the surface of a scalp or transcutaneously through the scalp. Through the electrodes, an EEG records voltage fluctuations resulting from the current within neurons of the brain. After the transmission of nerve signals through a sympathetic ganglion has been blocked (e.g., when the sympathetic ganglion is recruited) for 5 minutes to 45 minutes (e.g., 5 minutes, 10 minutes, 15 minutes, 20 minutes, 25 minutes, 30 minutes, 40 minutes), decreases in spectral edge frequency (SEF), beta to theta ratio (BTR), median frequency (MF), and beta to delta ratio (BDR) may be detected via EEG. The general operation of an EEG and how to detect decreases in SEF, BTR, MF, and/or BDR is known to those skilled in the art and, for the sake of brevity, will not be described in further detail herein. Monitoring the EEG of a patient (e.g., observing decreases in SEF, BTR, MF, and/or BDR) may inform a controller and/or a user (e.g., physician or patient) of the recruitment status of one or more nerves, such as, for example, the sympathetic ganglia (e.g., left stellate ganglion and/or right stellate ganglion). In some embodiments, a decrease of at least approximately 60%, at least approximately 65%, at least approximately 70%, at least approximately 75%, or at least approximately 80% in SEF, BTR, MF, and/or BDR may indicate recruitment of the sympathetic ganglia. In some embodiments, at least a 10% decrease in the bispectral index (BIS) of a patient, as monitored via EEF, may indicate recruitment of at least one sympathetic ganglion. In other embodiments, at least a 15% decrease or a 10-20% decrease in BIS may indicate recruitment of at least one sympathetic ganglion.

In one or more embodiments, monitoring the recruitment of a nerve (e.g. sympathetic ganglia) may include monitoring the pupil diameter and/or sclera color of a patient. When transmission of nerve signals through the sympathetic ganglia is blocked (e.g., when a sympathetic ganglion is recruited) a pupils of a patient may decrease in diameter. Further, the blocking of the transmission of nerve signals through the sympathetic ganglia (e.g., recruitment of the sympathetic ganglia) may cause one or more sclera of a patient to redden (i.e., change color from white to red or pink). Pupil contraction and sclera reddening may both be the result of increased blood flow to the eye as a result of the sympathetic ganglia recruitment. In some instances, blocking the transmission of nerve signals through the left stellate ganglion may cause the left pupil to contract (e.g., decrease in diameter) and/or the left sclera to redden. Additionally or in the alternative, blocking the transmission of nerve signals through the right stellate ganglion may cause the right pupil to contract (e.g., decrease in diameter) and/or the right sclera to redden. Monitoring the pupil size and/or sclera color of a patient may inform a controller and/or a user (e.g., physician or patient) of the recruitment status of one or more nerves, such as, for example, the sympathetic ganglia (e.g., left stellate ganglion and/or right stellate ganglion). In some embodiments, a difference of greater than or equal to 0.2 mm (e.g., greater than or equal to 0.3 mm or greater than or equal to 0.4 mm) in pupil diameter may indicate recruitment of at least one sympathetic ganglion. In other words, the measurement of one pupil of a patient as having a diameter 0.2 mm greater than the other pupil may indicate sympathetic ganglia recruitment.

In one or more embodiments, monitoring the recruitment of a nerve (e.g. sympathetic ganglia) may include monitoring one or more skin temperatures of a patient. After transmission of nerve signals through the sympathetic ganglia has been blocked (e.g., when a sympathetic ganglion is recruited) for 2 minutes to 30 minutes (e.g., 3 minutes, 5 minutes, 8 minutes, 10 minutes, 13 minutes, 15 minutes, 18 minutes, 20 minutes, 25 minutes, 30 minutes) the skin temperature on a limb and face of a patient may increase by 0.25° C. to 2° C. (e.g., 0.5° C. to 1.5° C.). In a healthy patient with normal nervous system function, limb and face temperature is a few degrees Celsius (e.g., 1-5° C.) below core body temperature. When the transmission of nerve signals through a sympathetic ganglion is blocked (e.g., the sympathetic ganglion is recruited), the skin temperature and face temperature of a patient may increase as blood flow increases to the head and limbs. Monitoring the skin temperature of the limbs and/or face of a patient (e.g., observing whether either or both skin temperatures increases) may inform a controller and/or a user (e.g., physician or patient) of the recruitment status of one or more nerves, such as, for example, the sympathetic ganglia (e.g., left stellate ganglion and/or right stellate ganglion).

In one or more embodiments, monitoring the recruitment of a nerve (e.g. sympathetic ganglia) may include monitoring the skin perspiration of a patient. Monitoring the skin perspiration may include monitoring either the rate of sweat or the density of sweat from or on one or more areas of skin. In at least one embodiment, skin perspiration is measured on both limbs of a patient. If either side of the patient has at least a 40% decrease (e.g., at least a 50% decrease or at least a 60% decrease) in skin perspiration rate or skin perspiration density compared to the other side, the sympathetic ganglia may be recruited.

In one or more embodiments, monitoring the recruitment of a nerve (e.g. sympathetic ganglia) may include monitoring blood circulation in the brain of a patient via a transcranial Doppler ultrasonogram. Generally, a transcranial Doppler ultrasonogram measures the velocity of blood flow through a brain's blood vessels by measuring the echoes of ultrasound waves passing from the blood vessels through the cranium. Like other types of Doppler ultrasonography, data or images can be generated based on measuring the Doppler effect of ultrasound waves introduced to the patient, influenced relative to the velocity of a fluid traveling within an anatomical space. After the transmission of nerve signals through a stellate ganglion has been blocked, the velocity of blood circulation in the brain may increase, which can be detected by a transcranial Doppler ultrasonogram. The general operation of a Doppler ultrasonogram is known to those skilled in the art and will not be described in further detail for sake of brevity. Monitoring the transcranial Doppler ultrasonogram of a patient (e.g., observing an increase in blood circulation velocity in the brain) may inform a controller and/or a user (e.g., physician or patient) of the recruitment status of one or more nerves, such as, for example, the sympathetic ganglia (e.g., left stellate ganglion and/or right stellate ganglion). For example, in some embodiments, a decrease in the blood flow in the middle cerebral artery by at least approximately 10% (e.g., at least approximately 15%) may be indicative of recruitment of the sympathetic ganglia. In other embodiments, an increase of at least approximately 15% (e.g., at least approximately 18% or at least approximately 20%) in cerebral perfusion pressure may be evidence of sympathetic ganglia recruitment. Further, a decrease of at least 7.5% (e.g., a decrease of at least 10% or a decrease of at least 15%) in zero flow pressure may indicate recruitment of the sympathetic ganglia.

Any of the previously described examples of monitoring recruitment of a nerve may be used alone or in combination with any other example of monitoring recruitment of a nerve. This monitoring may include monitoring the recruitment of the sympathetic ganglia (e.g., left stellate ganglion and/or right stellate ganglion). Further, in some embodiments, the methods of the present disclosure may include, based on the monitoring the recruitment of the sympathetic ganglia, adjusting the electrical signal from at least one electrode.

In one or more embodiments described herein, a system may include medical devices for performing the methods described in the disclosure. The system, as described below, may include components such as a catheter having a tubular member and one or more electrode assemblies, a signal generator to provide stimulation energy to the electrode assemblies, one or more sensors to sense the condition of the patient, and one or more control components allowing another device (including one or more hardware components and/or software components) or user (e.g., a physician, nurse, other healthcare provider, or a patient) to adjust the parameters of the transmitted electrical signal. The different embodiments of the various system components may be combined and used together in any logical arrangement. Furthermore, individual features or elements of any described embodiment may be combined with or used in connection with the individual features or elements of other embodiments. The various embodiments may further be used in different contexts than those specifically described herein. For example, the disclosed electrode structures may be combined or used in combination with various deployment systems known in the art for various diagnostic and/or therapeutic applications.

The systems and methods described in this disclosure may help to achieve at least one or more of the following to a patient: preventing, modulating, controlling, or treating brain injury. In some embodiments, the systems and methods herein may reduce brain injury via recruitment of the sympathetic ganglia. One or more electrical signals may be used to recruit one or more nerves and interfere with aberrant pain signals and help mitigate cell death. Electrical signals (e.g., pulsed electrical signals) transmitted via electrodes placed proximate to the sympathetic ganglia (e.g., in the esophagus near the left stellate ganglion or the right stellate ganglion) to recruit the sympathetic ganglia and temporarily block afferent signals. The transmitted electrical signal (e.g. the recruitment signal) may have a frequency of 100 hertz (Hz) to 100 kHz, including, for example, a frequency of 1 kHz to 50 kHz or 1 kHz to 30 kHz. Further, the recruitment signal may have an amplitude of 10 microamperes (µA) to 20 mA per phase. Other frequencies and amplitudes which may block conduction of axonal nerve signals without causing electrode corrosion or tissue damage are also contemplated.

Based on the monitoring of the recruitment of a sympathetic ganglion, the recruitment signal may be adjusted. For example, in one or more embodiments, a patient may be monitored for one or more indications of a sympathetic ganglion recruitment (e.g., recruitment of the left stellate ganglion and/or recruitment of the right stellate ganglion) as described above, via one or more sensors of the system. In response to a signal from one or more sensors that the sympathetic ganglion is recruited, the recruitment signal may be altered or ceased. For example, the frequency of the recruitment signal might be increased or decreased. Similarly, the amplitude of the recruitment signal might be increased or decreased. In response to a signal that the stellate ganglion is recruited, the recruitment signal might be reduced to a lower level or cease being transmitted. In other embodiments, a recruitment signal might be temporarily stopped if the system receives a signal that the stellate ganglion is recruited. Similarly, in response to a signal from one or more sensors that the sympathetic ganglion is not recruited, the recruitment signal may be altered. For example, the frequency and/or amplitude of the recruitment signal might be increased or decreased.

One or more components of systems described herein may include a plurality of electrodes (e.g., an esophageal catheter comprising a plurality of electrodes). The plurality of electrodes may be similarly shaped or have different shapes. For example, one or more electrodes may be curved, flat, straight-edged, rounded, planar, or other shape. In some embodiments, each of the plurality of electrodes may transmit a signal independently from the other electrodes of the plurality. In other embodiments, two or more electrodes of the plurality may be synced (e.g., configured to transmit coordinated signals). In some embodiments, in response to a signal that one of either the left stellate ganglion or the right stellate ganglion is recruited, the recruitment signal transmitted by one or more electrodes may be adjusted while the recruitment signal transmitted by one or more other electrodes may be not adjusted. For example, in response to a signal that the left stellate ganglion is recruited (when the right ganglion has not yet been recruited), the recruitment signal directed to the left stellate ganglion may be ceased or otherwise modified, while the recruitment signal directed to the right stellate ganglion may not be adjusted. Similarly, in response to a signal the right stellate ganglion is recruited (when the left ganglion has not yet been recruited), the recruitment signal directed to the right stellate ganglion may be ceased or otherwise modified, while the recruitment signal directed to the left stellate ganglion may not be adjusted.

FIG. 1A illustrates the anatomy of the head and neck and, in particular, the relative locations of the nasoesophageal cavity 110, oroesophageal cavity 115, and esophagus 120. In one or more embodiments an esophageal catheter 210, including one or more electrodes 220, may be inserted through a nasoesophgeal cavity 110 and into the esophagus 120. Although not shown in FIG. 1A, in some embodiments, esophageal catheter 210 may be inserted through oroesophageal cavity 115 into esophagus 120. Esophageal catheter 210 may be positioned such that one or more electrodes 220 are proximate to one or more nerves (e.g., sympathetic ganglia).

Referring to FIG. 1B, a system is shown according to one or more embodiments where esophageal catheter 210 is incorporated with or includes a feeding tube 230. According to some embodiments, a feeding tube 230 may travel from the exterior of a patient through the nasoesophgeal cavity 110 or an oroesophageal cavity 115 into the esophagus 120. One or more electrodes 220 of esophageal catheter 210 may be positioned in the esophagus 120 and proximate to one or more nerves (e.g., sympathetic ganglia). A distal end 240 of the feeding tube 230 may extend into the stomach 140 allowing for material to be passed from the exterior of the patient to the stomach 140 via feeding tube 230 without disturbing the placement of the one or more electrodes 220. Esophageal catheter 210 may be placed over an already inserted feeding tube 230, using the feeding tube 230 as a guide for the placement of esophageal catheter 210. In other embodiments, esophageal catheter 210 may be inserted next to and coupled to an already inserted feeding tube 230, e.g., as a side tube. In such embodiments, the esophageal catheter 210 and feeding tube 230 may occupy non-coaxial spaces within an esophagus 120. In some embodiments, electrodes 220 may be positioned, via a biocompatible adhesive or other suitable anchoring mechanism, on an outer surface of feeding tube 230. In further embodiments, esophageal catheter 210 may include a thermal probe to measure one or more internal temperatures.

In one or more embodiments, esophageal catheters 210 are readily applied to, or inserted into, the patient. The placement or insertion may be temporary, and catheter 210 may be easily removed from the patient at a later time without the need for surgery. In some embodiments, esophageal catheter may be left in the esophagus 120 of a patient for greater than or equal to 24 hours, greater than 7 days, greater than 10 days, greater than 14 days, greater than 21 days, greater than 28 days, or even greater than 30 days. For example, esophageal catheter 210 may be withdrawn once the patient is determined to no longer have an SAH and/or once the patient is no longer at risk, or is at a significantly reduced risk, for an SAH-mediated delayed CVS.

Figure 2A:
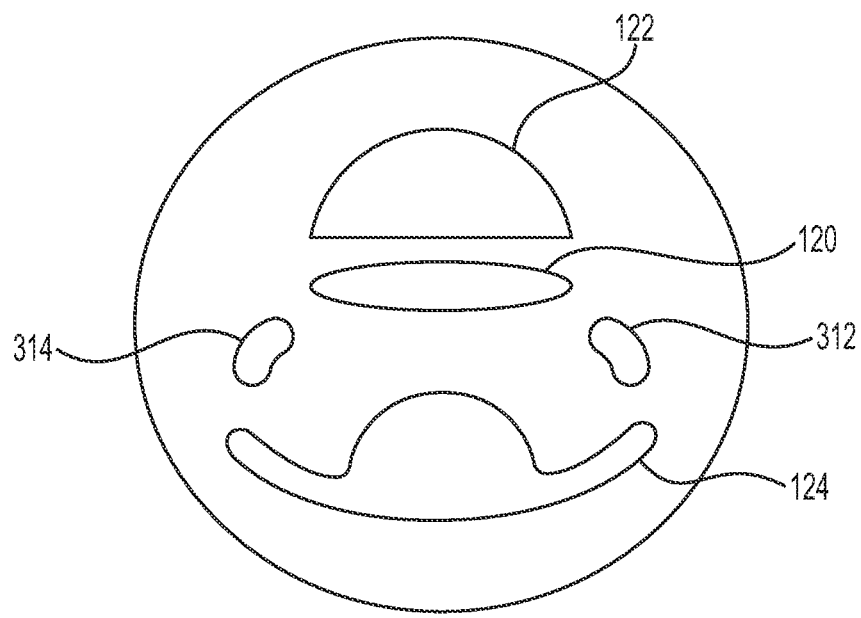
FIG. 2A illustrates an axial cross section including the anatomy of selected nerves, lumens, and bones in a person's neck, according to one or more embodiments of the present disclosure.

FIG. 2A further illustrates the anatomy of the neck and, in particular, the relative locations of esophagus 120, trachea 122, vertebra 124, left stellate ganglion 314 and right stellate ganglion 312. The cross-section shown in FIG. 2A is representative of any axial cross-section taken in the C4 to T2 region. The sympathetic ganglia includes the left stellate ganglion 314 and the right stellate ganglion 312. Further, each of the left stellate ganglion 314 and the right stellate ganglion 312 may have more than one branch. In some embodiments, vertebra 124 may be the C5 vertebra, the C6 vertebra, or the C7 vertebra.

Figure 2B:
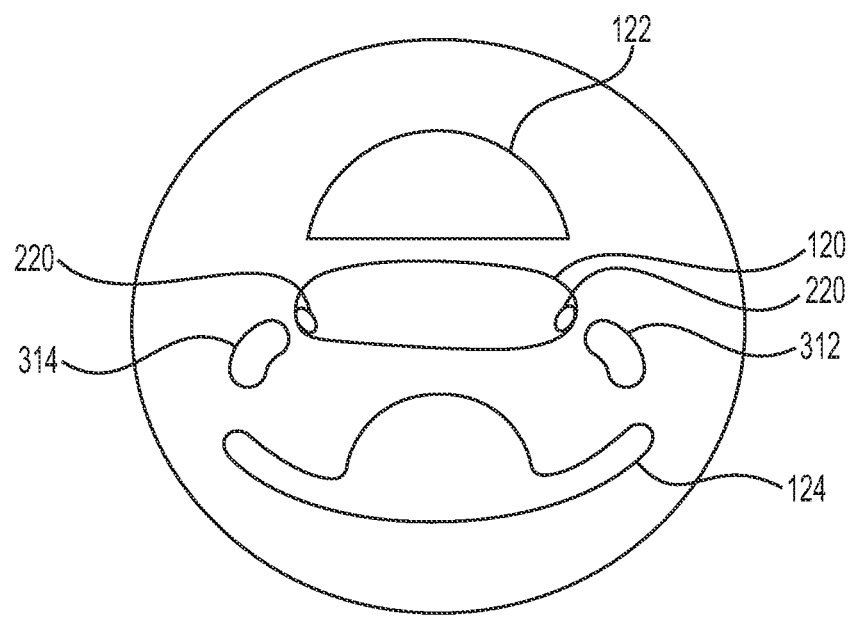
FIG. 2B illustrates the axial cross section shown in FIG. 2A, along with exemplary esophageal catheter electrodes placed within the esophagus.

Referring to FIG. 2B, the same axial cross section of the neck anatomy is taken as FIG. 2A, however FIG. 2B also depicts the placement of electrodes 220 of an esophageal catheter 210. As can be seen in FIG. 2B, esophagus 120 is maintained in an enlarged and distended state while esophageal catheter 210 is inserted therein. One or more electrodes 220 may be positioned proximate to the sympathetic ganglia, including, for example, left stellate ganglion 314 and/or right stellate ganglion 312. In some embodiments, the lumen of esophagus 120 may distend up to approximately 3 cm (e.g., up to approximately 2 cm) in the anterior-posterior dimension and up to approximately 5 cm (e.g., up to approximately 3 cm) in a lateral dimension.

Figure 3A:
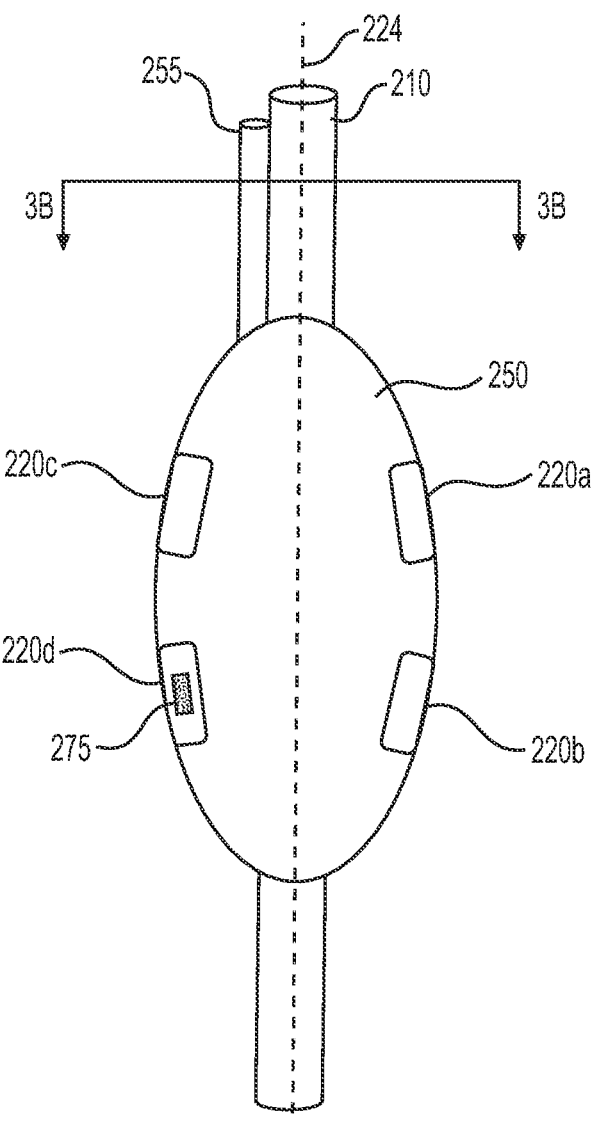
FIG. 3A illustrates a perspective view of an esophageal catheter, according to one or more embodiments of the present disclosure.

FIG. 3A illustrates an exemplary intermediate section of an esophageal catheter 210 including an inflation lumen 255, inflatable (expandable) member 250, electrodes 220, and feeding tube 230. The inflation member 250 runs along a length of the tubular esophageal catheter (e.g., occupying an intermediate section of the catheter length) and encompasses, encloses, or circumscribes the exterior of feeding tube 230, as shown in cross-section FIG. 3B. Inflation lumen 255 may extend proximally from the inflatable member 250 to the exterior of the patient, where it may be coupled to a controller and/or a fluid providing device or source. Fluid (e.g., air, saline, water) may be transported from the fluid providing device exterior of the patient to the inflatable member 250 via the inflation lumen 255. The transportation of fluid to the inflatable member 250 may cause the intermediate section of esophageal catheter 210 (e.g., the inflatable member 250) to expand from a contracted state to an expanded state. In one example, inflation member 250 may be a compliant or semi-compliant balloon. In other embodiments, an intermediate section may include an actuating member until tensile stress that is operable to expand the intermediate member upon movement and/or adjustment of the actuating member.

Figure 3B:
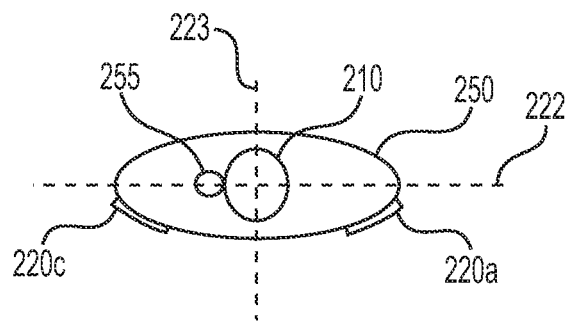
FIG. 3B illustrates a cross-sectional view depicting the esophageal catheter shown in FIG. 3A, along line 3B-3B of FIG. 3A.

Electrodes 220 may comprise traditional electrode metals such as, for example, stainless steel, gold, or an alloy including platinum and iridium. Each electrode may have an exposed surface area greater than or equal to 1.5 mm$^2$, such as, for example, greater than or equal to 2 mm$^2$, greater than or equal to 2.5 mm$^2$, greater than or equal to 3 mm$^2$, greater than or equal to 4 mm$^2$, or greater than or equal to 5 mm$^2$. Electrodes 220 may have a surface area such that a recruitment signal may be transmitted without damage to the electrode 220 or surrounding tissue. Electrodes 220 may be configured to have a surface area such that a transmitted charge density does not exceed therapeutic levels. Electrode 220a is positioned on a surface of the catheter opposite to electrode 220c (on an opposing side of longitudinal axis 224), and both electrodes 220a and 220c may be at the same axial position along longitudinal axis 224. Similarly, electrode 220b is positioned on a surface of the catheter opposite to electrode 220d (on opposing sides of longitudinal axis 224), and both electrode 220b and electrode 220d may be positioned at the same axial position along longitudinal axis 224 (and longitudinally staggered from electrodes 220a and 220c). Electrode 220a may be longitudinally aligned with electrode 220c, and electrode 220b may be longitudinally aligned with electrode 220d. All electrodes 220 may be independently controlled to transmit different electrical signals. In one or more embodiments, electrodes 220a and 220b are configured to transmit the same electrical signal. In some embodiments, two or more electrodes may be configured to be synced, where one electrode serves as the source of the electrical signal transmission and a second electrode may be the sink (e.g., the return electrode). In other embodiments, electrodes 220c and 220d may be configured to transmit the same electrical signal. As seen in FIG. 3B, catheter 210 includes a first lateral axis 222 (a major lateral axis), and a second lateral axis 223 (a minor lateral axis, e.g., an anteroposterior axis). First lateral axis 222 and second lateral axis 223 are both substantially perpendicular to longitudinal axis 224, and are substantially perpendicular to one another. Inflatable member 250 may have a larger dimension in the expanded state along first lateral axis 222 than along second lateral axis 223. Electrodes 220 may be positioned on inflatable member 250 on only one side of first lateral axis 222, while no electrodes 220 are positioned on inflatable member 250 on an opposing side of first lateral axis 250. This positioning may be based on the positions of left stellate ganglion 314 and right stellate ganglion 312 on only one lateral side of esophagus 120 as shown in FIGS. 2A and 2B. Electrodes 220 may be affixed or otherwise coupled to the exterior (outer surface) of esophageal catheter 210. In some embodiments, electrodes 220 may be embedded into esophageal catheter 210 and windows on the catheter may expose electrodes, allowing for a conductive path between electrodes 220 and surrounding tissue, including the esophagus in which catheter is inserted. Alternatively, electrodes could be printed onto the surface of the catheter by one of several known means (e.g. conductive inks, polymers) as described in U.S. Pat. No. 9,242,088, which is incorporated by reference herein. Further, the electrodes may be integrated into a flexible printed circuit, which can be attached to, or integrated into, the catheter. Insulation means known in the art may be used to ensure that the electrodes, and not any unwanted electrical elements, are exposed to direct contact with the patient. Esophageal catheter 210 may include rows of apertures or windows positioned proximally, medially and distally, such that when esophageal catheter 210 is inserted into an esophagus, at least one window may face, abut, or be positioned in the vicinity of the left stellate ganglion 314, at least one window may face, abut, or be positioned in the vicinity of the right stellate ganglion 312, and/or at least one window may face, abut, or be positioned in the vicinity of the sympathetic ganglia. Electrodes 220 may extend partially around the circumference of esophageal catheter 210. This electrode configuration may allow electrodes 220 to target a desired nerve for stimulation while minimizing application of electrical charge to undesired areas of the patient's anatomy (e.g., other nerves or the heart). The oral catheter may include one or more features (anchor, hooks, biocompatible adhesive, or the like) to secure or stabilize the catheter within the patient, and or the electrodes 220 at a specific location. Further, esophageal catheter 210 may be shaped to conform to the inner wall of the esophagus and position at least one electrode proximate the sympathetic ganglia. In some embodiments, esophageal catheter 210 is shaped to dispose at least two electrodes proximate to each of the left stellate ganglion and right stellate ganglion.

The dimensions of esophageal catheter 210 may be customized in accordance with the anatomy of a particular patient (e.g., different sizes of humans, pigs, chimpanzees, etc.). The catheter may have a length greater than or equal to 20 cm, such as for example, 25 cm, 30 cm, 35 cm, 40 cm, 45 cm, or 50 cm. Esophageal catheter 210 may also have an outer diameter less than or equal to 10 mm, such as for example, less than or equal to 8 mm, less than or equal to 6 mm, less than or equal to 5 mm, or less than or equal to 4 mm.

Esophageal catheter 210 may incorporate markings or other indicators on its exterior to help guide the positioning and orientation of the device. The catheter may also include internal indicators (e.g., radiopaque markers, contrast material such as barium sulfate, echogenic markers) visible by x-ray, ultrasound, or other imaging technique to assist with positioning esophageal catheter 210 in the desired location. In one or more embodiments, a radiopaque marker 275 may be placed on or adjacent to an electrode 220, as shown in FIG. 3A. In some embodiments, markers may correspond to positions of electrodes on only one side of lateral axis 222. Esophageal catheter 210 may include any combination of the features described herein. Accordingly, the features of the catheter are not limited to any one specific combination shown in the accompanying drawings.

Figure 4A:
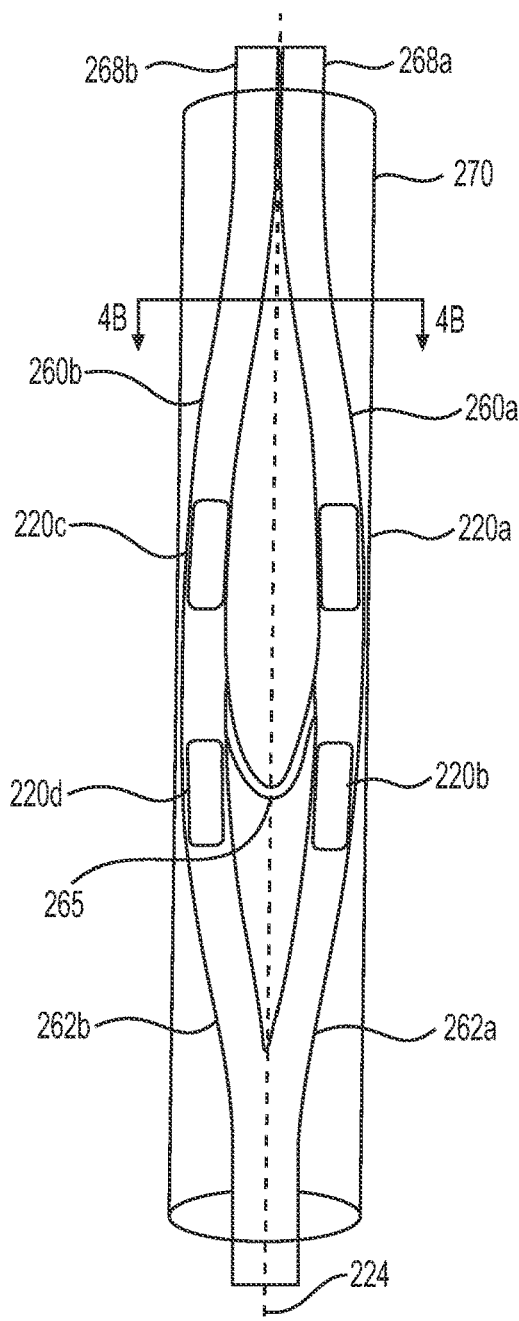
FIG. 4A illustrates a perspective view of an esophageal catheter in a contracted state, according to one or more embodiments of the present disclosure.
Figure 4B:
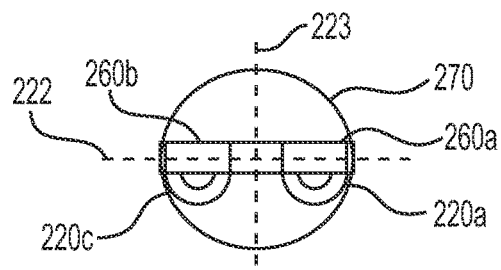
FIG. 4B illustrates a cross-sectional view depicting the esophageal catheter in a contracted state shown in FIG. 4A, along line 4B-4B of FIG. 4A.

As previously stated, aspects of one embodiment may be combined with aspects of one or more other embodiments. For example, the description of electrodes 220, their integration into esophageal catheter 210, and their placement proximate to sympathetic ganglia (e.g., left stellate ganglion 314 and/or right stellate ganglion 312) may be applicable to any esophageal catheter described herein. Referring now to FIGS. 4A-4B, an esophageal catheter 210 may include an intermediate section comprising two or more expandable arms 260 connected by a tether 265, which is slack in the contracted state shown in FIGS. 4A and 4B. In a contracted state, at least the intermediate section of catheter 210 is disposed within a sheath 270. Each arm 260 may include a joined end 262, a proximal end 268, and at least one electrode 220 positioned between the joined end 262 and the proximal end 268. Each joined end 262 may connect to the joined ends 262 of the other arms 260 at the distal end of catheter 210. For example, joined end 262a of arm 260a connects to joined end 262b of arm 262b by a weld or other suitable connection, as shown in FIG. 4A. Further, the proximal end 268 of each arm 260 is further displaced from the proximal end 268 of the other arms 260 when in an expanded state as compared to in a contracted state. For example, proximal end 268a of arm 260a is farther displaced from proximal end 268b of arm 260b when the intermediate section of esophageal catheter 210 expands to an expanded state, as shown in FIGS. 4A-4B.

Figure 4C:
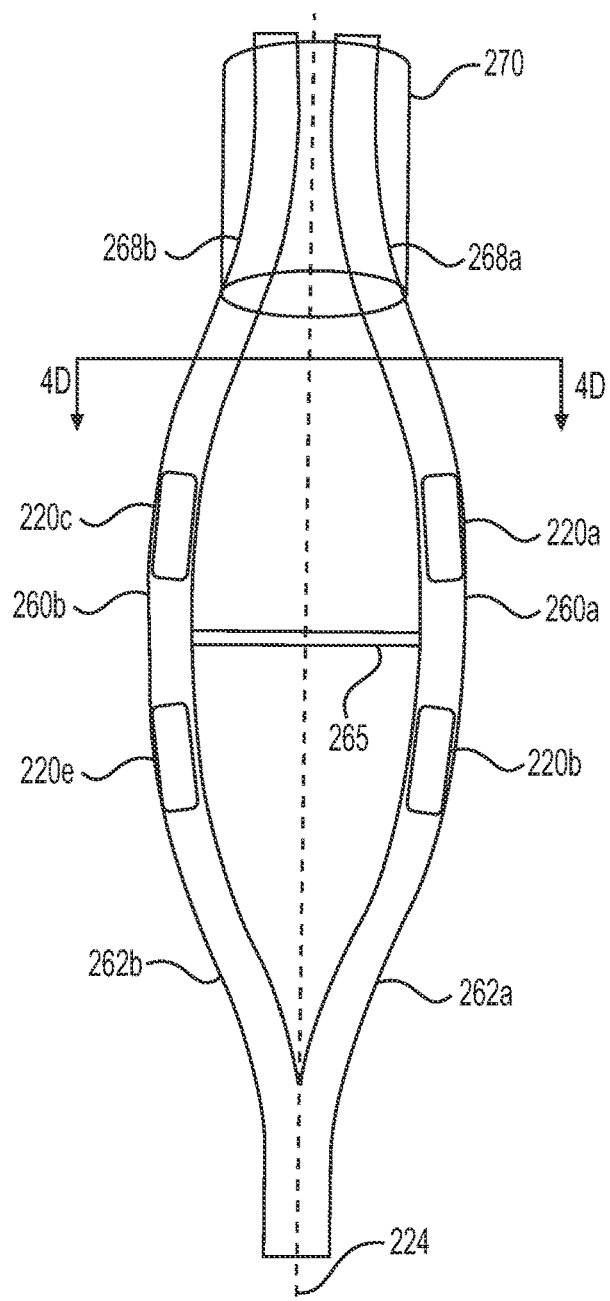
FIG. 4C illustrates a perspective view of the esophageal catheter of FIG. 4A in an expanded state.
Figure 4D:
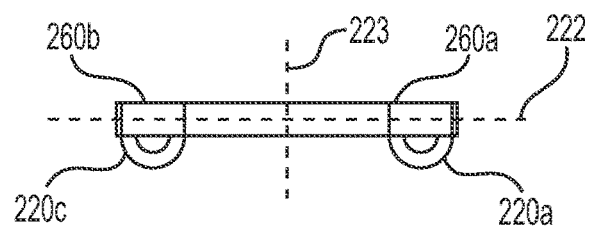
FIG. 4D illustrates a cross-sectional view depicting the esophageal catheter in an expanded state, along line 4D-4D of FIG. 4C.

Another exemplary intermediate section of esophageal catheter 210 shown in FIGS. 4A-4B is in a contracted state and disposed in a sheath 270. The shape of the catheter may be formed by heat setting the sheath 270, or by adding a shaped stainless steel wire or a shape memory nitinol wire or any other shape memory alloy. A shape-memory alloy may activate a helical shape of esophageal catheter 210 when heated to a temperature of 30° C. to 45° C., such as, for example, 37° C. When esophageal catheter 210 is deployed and removed from sheath 270 the proximal ends 268 of the intermediate section of the catheter may expand and displace farther apart, as shown in FIGS. 4C-4D. In other words, catheter 210 may be biased into the expanded state. As shown in FIG. 4C, the tether 265 is stretched taut, limiting the extent to which proximal ends 268 may radially separate and expand away from one another. This expanded helical shape may help anchor esophageal catheter 210 to the esophagus and/or to stabilize the catheter during nerve recruitment. The helical shape may position electrodes 220 at different radial positions within the esophagus and relative to target nerves such as for example the left stellate ganglion and/or right stellate ganglion. In some embodiments, all electrodes of an esophageal catheter 210 may be positioned on one side of the first lateral axis 222.

Referring now to FIG. 5A, an exemplary intermediate section of an esophageal catheter 210 in a contracted state is shown. FIGS. 5B-5C show the same intermediate section of esophageal catheter 210 in an expanded state. The catheter may include an intermediate section comprising two or more arms 260 on opposing sides of inflatable member 250 and an inflation lumen 255 connected to the inflatable member 250. Each arm 260 may include a joined end 262, a proximal end 268, and at least one electrode 220 positioned between the joined end 262 and the proximal end 268. Each joined end 262 may connect to the joined ends 262 of the other arms 260. For example, joined end 262a of arm 260a connects to joined end 262b of arm 262b, as shown in FIG. 5A. Further, the proximal end 268 of each arm 260 is further displaced from the proximal end 268 of the other arms 260 when in an expanded state as compared to in a contracted state. For example, proximal end 268a of arm 260a is farther displaced from proximal end 268b of arm 260b when the intermediate section of esophageal catheter 210 expands to an expanded state, as shown in FIGS. 5A-5B.

Inflatable member 250 may be inflated in a substantially similar manner as described above with respect to FIGS. 3A and 3B. The transportation of fluid to the inflatable member 250 may cause the intermediate section of esophageal catheter 210 (e.g., the inflatable member 250 and arms 260) to expand from a contracted state to an expanded state. In some embodiments, the electrodes 220 may be on only one side of lateral axis 222.

Figure 6:
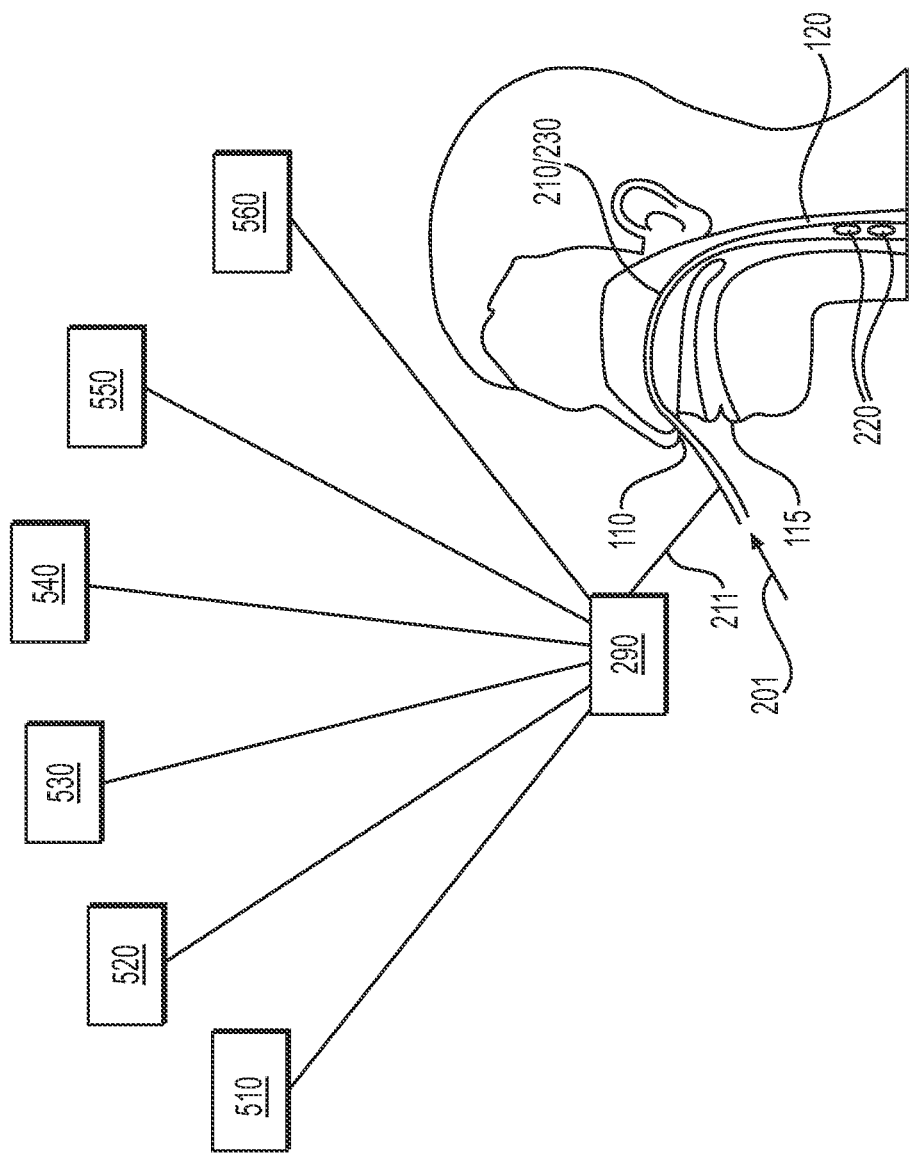
FIG. 6 illustrates a schematic view of a system having an esophageal catheter, a control unit, and one or more sensors, according various embodiments of the present disclosure.

FIG. 6 illustrates a block diagram of the various components of system. The system may include a controller 290, which may be part of any of the control units described herein. Each of the components of the system may be operably coupled to controller 290, and controller 290 may manage operation of electrodes 220 during nerve recruitment and control the gathering of information by various sensors (510, 520, 530, 540, 550, 560) during monitoring of recruitment. It should be understood that the various modules described herein may be part of a computing system and are separated in FIG. 6 for explanatory purposes only; it is not necessary for the modules to be physically separate.

Controller 290 may connect to the esophageal catheter 210 via a lead wire cable 211 and a connector. The lead wire cable may have a length greater than or equal to approximately a meter and the esophageal catheter may optionally include a feeding tube 230, with an inlet 201 for administration of substances including food stuff and nutrients. Controller 290 may connect to one or more sensors. For example, a sensor which detects palpebral droop 510, electrodes of an EEG 520, sensors which measure pupil diameter 530 (including, e.g., a pupilometer), a sensor which detects sclera color change 540, one or more skin temperature sensors 550, or sensors connected to a transcranial Doppler ultrasonogram 560, as described herein. In some embodiments, one or more sensors configured to detect a physiological parameter (e.g., palpebral slump, pupil diameter, sclera color) may include a camera or other imaging device, one or more photo filers, image recognition/processing software, and/or an algorithm for determining the state of a physiological parameter based on a captured image. For example, an infrared camera may be used to monitor skin temperatures over time and one or more image recognition software components or algorithms may recognize or detect one or more patterns in the fluctuation of skin temperature. In further embodiments, one or more sensors for detecting skin temperature may include one or more triple-patch electrodes placed on the forehead and/or one or more limbs. In some embodiments, an electrode, functioning as a sensor, may measure intraocular pressure. In still other embodiments, one or more electrodes or collection vesicles may be placed near or on the skin to measure skin perspiration rate and/or perspiration density.

The one or more sensors may transmit various signals to the operator 290, influencing the operator 290 to adjust the electrical signal transmitted by one or more electrodes 220. For example one or more sensors may transmit a signal to the operator 290 and based on that signal, the operator 290 may induce one or more electrodes to adjust the amplitude or frequency of the transmitted electrical signal.

Figure 7:
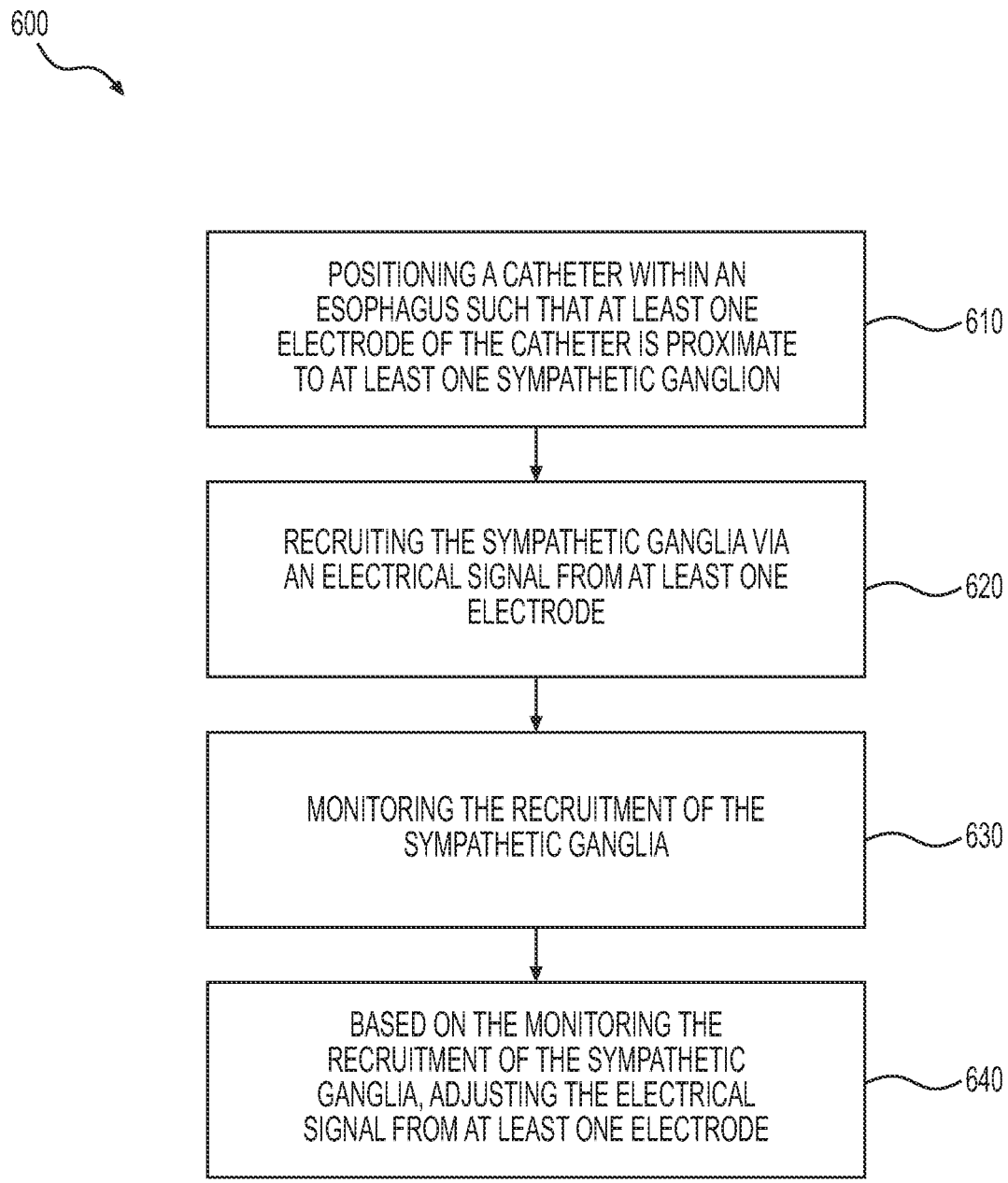
FIG. 7 is a flowchart of a method according to an embodiment of the present disclosure.

FIG. 7 depicts a flow chart of an exemplary method 600 of treatment, according to the present disclosure. In the discussion below of exemplary methods and flow charts, reference may be made to the reference numerals detailed in FIGS. 1A-6. In one or more embodiments, a method of treatment may include positioning a catheter 210 within an esophagus 120 such that at least one electrode 220 of the catheter 210 is proximate to at least one sympathetic ganglion (e.g., left stellate ganglion 314 and/or right stellate ganglion 312) (step 610). The method 600 may further include recruiting the sympathetic ganglia (e.g., left stellate ganglion 314 and/or right stellate ganglion 312) via an electrical signal from at least one electrode (step 620). In some embodiments, the method 600 may further include monitoring the recruitment of the sympathetic ganglia (e.g., left stellate ganglion 314 and/or right stellate ganglion 312) (step 630). This monitoring may optionally be done by one or more of a sensor which detects palpebral droop 510, electrodes of an EEG 520, sensors which measure pupil diameter 530, a sensor which detects sclera color change 540, one or more skin temperature sensors 550, or sensors connected to a transcranial Doppler ultrasonogram 560. The method 600 may further include, based on the monitoring the recruitment of the sympathetic ganglia (e.g., left stellate ganglion 314 and/or right stellate ganglion 312), adjusting the electrical signal from at least one electrode 220 (step 640).

In some embodiments, recruitment of the sympathetic ganglia via high-frequency electrical signals using temporary intra-esophageal electrodes may provide for a simpler, more convenient, and safer method to transiently and reversibly block the transmission of sympathetic nerve signals than the current standard of care (e.g., percutaneous hypodermic needle injection of anesthesia.

One or more esophageal catheters described herein may have features to meet unique anatomical and electrical requirements. Intra-esophageal lumens, such as, for example, nasogastric feeding tubes or diaphragmatic EMG sensing leads used for neurally adjusted ventilator assist may be inserted in patients and safely left in the patient for days and may be removed without harm to the patient. Esophageal catheters described herein may minimize the conduction distance from the stimulation source electrodes to the target sympathetic neurons, maximizing the field strength directed in a lateral and dorsal direction towards target tissue. This may minimize unwanted stimulation of other neural structures, such as, for example, the recurrent laryngeal nerves which are located more medially and anteriorly, and may minimize the risk of causing mechanical or electrical damage to the esophageal wall or neural structures.

The amplitude of the electrical signal transmitted by one or more electrodes of an esophageal catheter (e.g., a recruitment signal) may be graded to select which fibers in a nerve are recruited, based on fiber size and fiber location. Recruitment of a nerve may be suddenly onset (e.g., may occur in less than or equal to 10 ms, such as, less than or equal to 5 ms), may be rapidly released, and/or may persist minutes or hours after recruitment signal is ceased. For example, in some embodiments, a recruitment signal lasting one minute in duration may recruit at least one sympathetic ganglion for at least approximately 30 minutes.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A system comprising:
    an esophageal catheter including at least one electrode;
    one or more sensors for measuring a peripheral blood flow; and
    a controller in communication with the at least one electrode and the one or more sensors;
    wherein, upon receiving a first signal from the one or more sensors based on the peripheral blood flow, the controller induces the at least one electrode to transmit a recruiting signal that recruits the sympathetic ganglion.

2. The system of claim 1, wherein upon receiving a second signal from the one or more sensors, the controller induces the at least one electrode to adjust one or more of an amplitude or a frequency of the recruiting signal.

3. The system of claim 1, wherein upon receiving a second signal from the one or more sensors, the controller induces the at least one electrode to cease transmitting the recruiting signal.

4. The system of claim 1, wherein the at least one electrode is at least one first electrode, the sympathetic ganglion is a left stellate ganglion, the recruiting signal is a first recruiting signal, and upon receiving the first signal from the one or more sensors, the controller also induces at least one second electrode to transmit a second recruiting signal that recruits a right stellate ganglion.

5. The system of claim 1, wherein the recruiting signal is pulsed, and has a frequency of 100 Hz to 100 kHz and an amplitude of 10 μm to 20 mA.

6. The system of claim 1, wherein recruiting the sympathetic ganglion includes blocking transmission of nerve signals along the sympathetic ganglion.

7. The system of claim 1, wherein the catheter includes an intermediate section operable to radially expand from a contracted state to an expanded state.

8. The system of claim 1, wherein the catheter further includes a feeding tube.

9. The system of claim 1, wherein the peripheral blood flow is measured using a transcranial Doppler ultrasonogram.

10. A system comprising:
    an esophageal catheter including a plurality of electrodes, where a first electrode of the plurality of electrodes is positioned on a surface of the catheter and opposite a second electrode of the plurality of electrodes, where the first electrode and second electrode are positioned at a same axial level;
    a first sensor for measuring a left pupil diameter;
    a second sensor for measuring a right pupil diameter; and
    a controller in communication with the at least one electrode and the first and second sensors;
    wherein, upon receiving a first signal from the first sensor based on the left pupil diameter, the controller induces the first electrode to transmit a first recruiting signal that recruits a left stellate ganglion; and
    upon receiving a second signal from the second sensor based on the right pupil diameter, the controller induces the second electrode to transmit a second recruiting signal that recruits a right stellate ganglion.

11. The system of claim 10, wherein recruiting the left stellate ganglion includes blocking transmission of nerve signals along the left stellate ganglion, and/or recruiting the right stellate ganglion includes blocking transmission of nerve signals along the right stellate ganglion.

12. The system of claim 10, wherein the catheter includes an intermediate section operable to radially expand from a contracted state to an expanded state, and wherein the first electrode and the second electrode are disposed within the intermediate section of the catheter.

13. The system of claim 12, wherein the intermediate section comprises an inflatable member.

14. The system of claim 12, wherein, when the intermediate section of the catheter is in the expanded state, the first electrode is farther displaced from the second electrode, as compared to when the intermediate section of the catheter is in the contracted state.

15. A system comprising:
    an esophageal catheter including at least one electrode;
    one or more sensors; and
    a controller in communication with the at least one electrode and the one or more sensors;
    wherein upon receiving a first signal from the one or more sensors, or a user, the controller induces the at least one electrode to transmit a recruiting signal to a sympathetic ganglion, where the recruiting signal is pulsed, and has a frequency of 100 Hz to 100 kHz and an amplitude of 10 μA to 20 mA; and
    upon receiving a second signal from the one or more sensors, or the user, the controller induces the at least one electrode to adjust the frequency of the recruiting signal, the amplitude of the recruiting signal, or both.

16. The system of claim 15, wherein the catheter includes an intermediate section operable to radially expand from a contracted state to an expanded state;
    the at least one electrode includes a first electrode positioned within the intermediate section of the catheter and a second electrode positioned within the intermediate section of the catheter; and when the intermediate section is in the expanded state, the first electrode is farther displaced from the second electrode, as compared to when the intermediate section of the catheter is in the contracted state.

17. The system of claim 16, wherein the catheter further includes a feeding tube.

18. The system of claim 15, wherein the one or more sensors are configured to measure a blood circulation velocity in a blood vessel in a brain.

* * * * *